US006353009B1

(12) United States Patent
Fujiwara et al.

(10) Patent No.: US 6,353,009 B1
(45) Date of Patent: Mar. 5, 2002

(54) METHOD FOR THE TREATMENT AND PREVENTION OF HYPERURICEMIA

(75) Inventors: Toshihiko Fujiwara, Ebina; Koichi Iwasaki, Chiba; Hiroyoshi Horikoshi, Funabashi, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/195,031

(22) Filed: Nov. 18, 1998

(30) Foreign Application Priority Data

Nov. 25, 1997 (JP) .............................. 9-323182

(51) Int. Cl.$^7$ ...................... A61K 31/425; A61K 31/22; A61K 31/42

(52) U.S. Cl. ....................... 514/365; 369/549; 369/376; 369/377

(58) Field of Search ................................ 514/365, 369, 514/376, 377, 378, 396, 359, 370, 546

(56) References Cited

U.S. PATENT DOCUMENTS

| | | | |
|---|---|---|---|
| 4,287,200 A | 9/1981 | Kawamatsu et al. | 514/369 |
| 4,340,605 A | 7/1982 | Kawamatsu et al. | 427/126.3 |
| 4,438,141 A | 3/1984 | Kawamatsu et al. | 514/236.8 |
| 4,444,779 A | 4/1984 | Kawamatsu et al. | 514/342 |
| 4,461,902 A | 7/1984 | Kawamatsu et al. | 548/183 |
| 4,572,912 A | 2/1986 | Yoshioka et al. | 514/369 |
| 4,687,777 A | 8/1987 | Meguro et al. | 514/342 |
| 4,703,052 A | 10/1987 | Eggler et al. | 514/369 |
| 4,725,610 A | 2/1988 | Meguro et al. | 514/369 |
| 4,841,076 A | 6/1989 | Kitagawa et al. | 549/401 |
| 4,873,255 A | 10/1989 | Yoshioka et al. | 514/337 |
| 4,897,393 A | 1/1990 | Iijima et al. | 548/183 |
| 4,897,405 A | 1/1990 | Alessi et al. | 514/360 |
| 4,918,091 A | 4/1990 | Cantello et al. | 514/233.8 |
| 4,948,900 A | 8/1990 | Iijima et al. | 514/183 |
| 5,002,953 A | 3/1991 | Hindley | 514/275 |
| 5,061,717 A | 10/1991 | Clark et al. | 514/342 |
| 5,120,754 A | 6/1992 | Clark et al. | 514/369 |
| 5,132,317 A | 7/1992 | Cantello et al. | 514/369 |
| 5,155,114 A * | 10/1992 | Shiokawa et al. | 514/300 |
| 5,194,443 A | 3/1993 | Hindley | 514/367 |
| 5,223,522 A | 6/1993 | Clark et al. | 514/369 |
| 5,232,925 A | 8/1993 | Hindley | 514/272 |
| 5,260,445 A | 11/1993 | Hindley | 514/183 |

FOREIGN PATENT DOCUMENTS

| | | |
|---|---|---|
| EP | 0 139 421 A | 5/1985 |
| EP | 0332332 A | 9/1989 |
| EP | 0604983 A | 7/1994 |
| EP | 604983 | 7/1994 |
| EP | 0676398 A | 10/1995 |
| EP | 676398 | 10/1995 |
| EP | 0708098 A | 4/1996 |
| EP | 708098 | 4/1996 |
| EP | 745600 | 12/1996 |
| EP | 0745600 A | 12/1996 |
| JP | 4-69383 A | 3/1992 |
| JP | 6-211657 | 8/1994 |
| WO | WO 89/08651 | 9/1989 |
| WO | WO 91/07107 | 5/1991 |
| WO | WO 92/02520 | 2/1992 |
| WO | WO 94/10433 | 1/1994 |
| WO | WO 95/07694 | 3/1995 |
| WO | WO 95/18125 | 7/1995 |
| WO | WO 98/58658 | 12/1998 |

OTHER PUBLICATIONS

M. Modan et al., "Elevated Serum Uric Acid—a Facet of Hyperinsulinaemia", *Diabetologia*, 30(9), pp. 713–718 (1987).
Facchini et al., "Relationship Between Resistance to Insulin– Mediated Glucose Uptake, Urinary Uric Acid Clearance, and Plasma Uric Concentration", *JAMA*, 266(21), pp. 3008–3011 (1991).
R.E. Buckingham et al, "Peroxisome Proliferator–Activated Receptor–γ Agonist, Rosiglitazone, Protects Against Nephropathy and Pancreatic Islet Abnormalities in Zucker Fatty Rats", *Diabetes*, vol. 47 (8), pp.1326–1334 (Aug. 1998).
A. Tiengo, "La sindrome plurimetabolica: aspetti patogenetici e terapeutici", *Gironale Italiano Di Diabetilogia*, vol. 15, pp. 115–130 (1995).
T. Yoshimoto et al, "Antihypertensive and vasculo– and renoprotective effects of pioglitazone in genetically obese diabetic rats", *American Journal of Physiology*, 272 (6 PT 1), pp. E989–E996 (Jun. 1997).
J. Conn et al, "Insulin resistance in cardiovascular disease", *British Journal of Cardiology*, vol. 5, Issue 6, pp. 329–336 (Jun. 1998).
Fukuda et al, "CS–045, a New Oral Antidiabetic Agent Prevents the Development of Cyclophosphamide–induced Diabetes in NOD Mice", *J. Japan Diab. Soc.*, 37(2), 127–130 (1994).
Kuzuya et al, "An Early Phase II Clinical Trial of a New Oral Hypoglycemic Drug, CS–045, in Patients with Non– Insulin Dependent Diabetes Mellitsu", *Journal of Clinical Therapeutics & Medicines*, 9, Suppl. 3, 12–14 (1993).
Masako Iwatani, "Uric acid metabolism and insulin resistance in hyperuricemia, gout, and non–insulin–dependent diabetes mellitus", *Diabetes*, 40, Suppl. 1, 239 (1997).
Taniguchi et al, "Obesity and hyperlipidemia in gout", *Sogo Rinsho*, 46(8), 2128 (1997:8).
*Mebio*, 14(9), 90–96 (1997).
R.L. Chaiken, M. Eckert–Norton, R. Pasmantier, G. Boden, I. Ryan, R.A. Gelfand, H.E. Lebovitz, "Metabolic Effects of Darglitazone, an Insulin Sensitizer, in NIDDM Subjects", *Diabetologia*, 38, 1307–1312 (1995).

(List continued on next page.)

*Primary Examiner*—Theodore J. Criares
(74) *Attorney, Agent, or Firm*—Frishauf, Holtz, Goodman, Langer & Chick, P.C.

(57) ABSTRACT

Insulin sensitivity enhancers, such as troglitazone, have the ability to treat and/or prevent hyperuricemia and may thus be used for the therapy or prophylaxis of such diseases as gout, urinary calculus, hyperuricemic nephropathy and Lesch-Nyhan syndrome.

27 Claims, No Drawings

OTHER PUBLICATIONS

Robert M. Cohn, Karl S. Roth, *Metabolic Disease—A Guide to Early Recognition*, (1986), p. 562, 568–569.

E. Madyanov, "Relation between Uremia and Some Clinic and Metabolic Association of Diabetes in the Stage of Diabetes Continuation", Author's Abstract of PhD dissertation, p. 13, lines 3–11, Samara, (1992).

M.C. Balabolkin, *Diabetes 100 Q & A.*, pp. 48–49, N., (1992).

* cited by examiner

METHOD FOR THE TREATMENT AND PREVENTION OF HYPERURICEMIA

FIELD OF THE INVENTION

1. Background to the Invention

The present invention relates to a composition and method for the treatment or prevention of hyperuricemia, in which the active agent is an insulin-resistance improving substance, commonly referred to as "insulin sensitivity enhancers".

2. Background Information

Hyperuricemia is a disease characterized by an abnormally high level of uric acid in the plasma: Plasma is saturated with uric acid at 7.0 mg/dl, and, if the level of uric acid in the blood reaches or exceeds this level because of a metabolic disorder involving uric acid, the resulting condition is called "hyperuricemia". When the concentration of uric acid in the blood exceeds a certain level, uric acid precipitates as monosodium urate and may deposit in various tissues, such as the cavitas articulare or kidney. This deposition may cause gout, renal disorders or angiopathy. Hyperuricemia may be caused by reduced excretion of uric acid, by its excessive production or by a combination of both. It may also result from other diseases, such as an enzymatic abnormality in the purine metabolism. These are all so-called "primary causes". Other diseases, such as disorders of the hemocytopoietic organs and renal disorders, and administration of a medicament, such as pyrazinamide or thiazide, may also result in hyperuricemia, and are "so-called secondary causes".

Examples of diseases caused by hyperuricemia include gout (including acute gouty arthritis and chronic tophaceous arthritis), urinary calculus, hyperuricemic nephropathy (chronic gouty nephropathy, acute hyperuricemic nephropathy) and Lesch-Nyhan syndrome.

Initial treatment of the symptoms of hyperuricemia, particularly gout, may be by the administration of an analgesic agent, such as colchicine, and/or an analgesic anti-inflammatory, such as indomethacin. It is common practice to treat the longer term problem of hyperuricemia by control of the diet, for example by limiting the intake of alcohol or by controlling intake of calories. However, if this dietetic treatment does not work sufficiently well, the disease may be treated by the administration of drugs, for example by the prophylactic administration of an analgesic agent, such as colchicine, or by means of a uric acid excretion stimulator, such as probenecid, sulfinpyrazone, ketophenylbutazone, bucolome or benzbromarone, or a uric acid synthesis inhibitor, such as allopurinol.

In recent years, insulin sensitivity enhancers have been developed for the prevention or treatment of diabetes. The term "insulin sensitivity enhancer" as used herein means a compound which can bring about an improvement in the impaired action of insulin in spite of the existence of endogenous insulin. A wide range of compounds is embraced by the term "insulin sensitivity enhancer". Typical examples include various thiazolidinedione compounds, oxazolidinedione compounds, isoxazolidinedione compounds and oxadiazolidinedione compounds. They are described, for example, in: WO 94/01433 (=Japanese Patent Application Kokai No. Hei 6-80667), Japanese Patent Application Kokai No. Hei 4-69383, WO 92/02520 (=Japanese Language Kokai Publication (PCT) No. Hei 6-500538), WO 91/07107 (=Japanese Patent Application Kokai No. Hei 3-170478=Japanese Patent Publication No. Hei 7-8862), U.S. Pat. No. 5,132,317 (=Japanese Patent Application Kokai No. Hei 3-90071), U.S. Pat, No. 4,897,405 (=Japanese Patent Application Kokai No. Hei 2-292272), WO 89/08651 (=Japanese Patent Application Kokai No. Hei 1-272574), U.S. Pat. Nos. 5,061,717, 5,120,754, 5,223,522 (=Japanese Patent Application Kokai No. Hei 1-272573), U.S. Pat. Nos. 5,002,953, 5,194,443, 5,232,925, 5,260,445 (=Japanese Patent Application Kokai No. Hei 1-131169), U.S. Pat. No. 4,918,091 (=Japanese Patent Application Kokai No. Sho 64-13076), U.S. Pat. Nos. 4,897,393, 4,948, 900 (=Japanese Patent Application Kokai No. Sho 64-56675 =Japanese Patent Publication No. Hei 5-5832), U.S. Pat. No. 4,873,255 (=Japanese Patent Application Kokai No. Sho 64-38090), U.S. Pat. No. 4,703,052 (=Japanese Patent Application Kokai No. Sho 61-271287= Japanese Patent Publication No. Hei 5-86953), U.S. Pat. No. 4,687,777(=Japanese Patent Application Kokai No. Sho 61-267580 =Japanese Patent Publication No. Hei 5-31079), U.S. Pat. No. 4,725,610 (=Japanese Patent Application Kokai No. Sho 61-85372=Japanese Patent Publication No. Hei 5-66956), U.S. Pat. No. 4,572,912 (=Japanese Patent Application Kokai No. Sho 60-51189=Japanese Patent Publication No. Hei 2-31079), U.S. Pat. No. 4,461,902 (=Japanese Patent Application Kokai No. Sho 58-118577= Japanese Patent Publication No. Hei 2-57546), U.S. Pat. Nos. 4,287,200, 4,340,605, 4,438,141, 4,444,779 (=Japanese Patent Application Kokai No. Sho 55-22636= Japanese Patent Publication No. Sho 62-42903), EP 0 708 098A (Japanese Patent Application Kokai No. Hei 9-48779), EP 0 676 398A (=Japanese Patent Application Kokai No. Hei 7-330728), WO 95/18125, EP 0 745 600A, EP 0 332 332A (=Japanese Patent Application Kokai No. Hei 1-272574) and EP 0 604 983A (=Japanese Patent Application Kokai No. Hei 6-247945).

For example, 5-[4-(6-hydroxy-2,5,7,8-tetramethylchroman-2-ylmethoxy)benzyl]-thiazolidine-2,4-dione (which will hereinafter be called "troglitazone") is a thiazolidine derivative having the ability to enhance the action of insulin and is known for the treatment and/or prevention of diabetes [Fujiwara et al., "Diabetes", 37, 1459 (1988); Hofmann C. A. et al., "Diabetes Care", 15, 1075 (1992)]. It has also been reported that the compound has an antioxidant action and is therefore useful as a treatment for insulin-dependent diabetes mellitus (Type I diabetes: IDDM) ["Tonyobyo (Diabetes)", 37(2), 127–129 (1994)].

It has not, however, previously been reported that any of the above compounds are useful for the treatment or prevention of hypenrnicemia.

There is, for example, a report based on clinical examination values concerning the relationship between the administration of CS-045 (=troglitazone) and uric acid. According to this report, before the administration of troglitazone, the uric acid level is 4.7±1.7, which decreases slightly to 4.4±1.4 after administration. This decrease is within the normal changes to be expected, and there is no suggestion that the administration of troglitazone is effective for the treatment or prevention of hyperuricemia ["Rinsho Iyaku (Clinical Medicine)", 9, Suppl.3 (July issue), 14 (1993)].

There have also been reports on the relationship between hyperuricemia and insulin resistance. They only suggest the relationship and do not make any suggestion that an insulin sensitivity enhancer is effective for the treatment or prevention of hyperuricemia ["Tonyobyo (Diabetes)", 40, an extra number, 239, 2P041 (1997), "Sougo Rinsho (Clinic All-round)", 46(8), 2128–2130 (1997) and "Mebio", 14(9), 90–96 (1997)].

It has been reported, for example, that 1-(3-bromobenzo [b]furan-2-ylsulfonyl)hydantoin (Japanese Patent Application Kokai No. Hei 6-211657) or benzopyran derivatives (Japanese Patent Application Kokai No. Sho 63-107971), such as ethyl {[5-chloro-3-(2-methylphenyl)-4-oxo-4H-1-benzopyran-7-yl]oxy}acetate, are effective for the prevention and treatment of hyperuricemia, but they are utterly different in structure from the compounds of the present invention.

We have now, most surprisingly, discovered that certain classes of compound which are insulin sensitivity enhancers also have the ability to treat and/or prevent hyperuricemia.

BRIEF SUMMARY OF THE INVENTION

An object of the present invention is to provide a method for the treatment or prevention of hyperuricemia.

A further object of the present invention is to provide a composition for the treatment or prevention of hyperuricemia.

Other objects and advantages of the present invention will become apparent as the description proceeds.

The present invention thus provides a method for the treatment or prevention of hyperuricemia in a mammal suffering from hyperuricemia, which comprises administering to said mammal an amount of an insulin sensitivity enhancer effective to reduce or prevent hyperuricemia.

The invention also provides a composition for the treatment or prevention of hyperuricemia in a mammal suffering from hyperuricemia, which comprises an effective amount of an insulin sensitivity enhancer.

DETAILED DESCRIPTION OF THE INVENTION

In particular, the insulin sensitivity enhancers employed in the present invention are preferably selected from the group consisting of thiazolidinedione compounds, iminothiazolidinone compounds, diiminothiazolidine compounds, thioxothiazolidinone compounds, iminotriazole compounds, oxazolidinedione compounds, isoxazolidinedione compounds and oxadiazolidinedione compounds, preferably the thiazolidinedione compounds. Also included are pharmaceutically acceptable salts of these compounds.

Examples of the insulin sensitivity enhancers which may be used in the present invention are as follows:

(I) Japanese Patent Application Kokai No. Sho 60-51189 (Japanese Patent Publication No. Hei 2-31079), U.S. Pat. No. 4,572,912 and European Patent Publication No. 139421A describe:

(1) thiazolidine derivatives represented by the following formula (I):

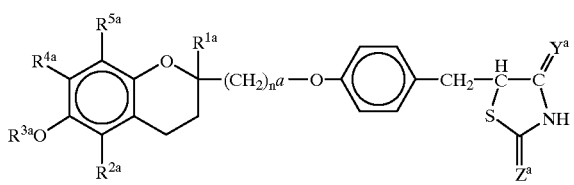

(I)

wherein:
  $R^{1a}$ and $R^{2a}$ are the same or different and each represents a hydrogen atom or an alkyl group having from 1 to 5 carbon atoms;
  $R^{3a}$ represents a hydrogen atom, an aliphatic acyl group having from 1 to 6 carbon atoms, a cycloalkylcarbonyl group having from 6 to 8 carbon atoms, a benzoyl or naphthoyl group which is unsubstituted or is substituted by at least one substituent selected from the group consisting of substituents χ, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group substituted with at least one halogen atom, a cinnamoyl group, an alkoxycarbonyl group having from 2 to 7 carbon atoms or a benzyloxycarbonyl group;
    said substituent χ is an alkyl group having from 1 to 4 carbon atoms, an alkoxy group having from 1 to 4 carbon atoms, a hydroxy group, a halogen atom, an amino group, a monoalkylamino group having from 1 to 4 carbon atoms, a dialkylamino group having from 1 to 4 carbon atoms in each alkyl group or a nitro group;
  $R^{4a}$ and $R^{5a}$ are the same or different and each represents a hydrogen atom, an alkyl group having from 1 to 5 carbon atoms or an alkoxy group having from 1 to 5 carbon atoms, or $R^{4a}$ and $R^{5a}$ together represent an alkylenedioxy group having from 1 to 4 carbon atoms;
  $Y^a$ and $Z^a$ are the same or different and each represents an oxygen atom or an imino group; and
  $n^a$ represents an integer of from 1 to 3;
and pharmaceutically acceptable salts thereof.

In the compounds of formula (I), details, such as the definitions of $R^{1a}$, $R^{2a}$, $R^{3a}$, $R^{4a}$, $R^{5a}$, $Y^a$, $Z^a$ and $n^a$, the kinds of pharmaceutically acceptable salt, the process for preparing the compounds of formula (I), examples of the compound and preparative examples are described in Japanese Patent Application Kokai No. Sho 60-51189 (Japanese Patent Publication No. Hei 2-31079), U.S. Pat. No. 4,572,912 and European Patent Publication No. 139421A, the disclosures of which are incorporated herein by reference.

More specifically, where $R^{1a}$, $R^{2a}$, $R^{4a}$, or $R^{5a}$ represents an alkyl group, this may be a straight or branched chain alkyl group having from 1 to 5, carbon atoms, and examples include the methyl, ethyl, propyl, isopropyl, butyl, isobutyl, sec-butyl, t-butyl, pentyl, 1-methylbutyl, 2-methylbutyl, 3-methylbutyl, 1-ethylpropyl and 2-ethylpropyl groups. Of these, we prefer those alkyl groups having from 1 to 4 carbon atoms, most preferably the methyl group.

Where $R^{3a}$ represents an aliphatic acyl group having from 1 to 6 carbon atoms, this may be a straight or branched chain group. Specific examples include the formyl, acetyl, propionyl, butyryl, isobutyryl, pivaloyl, valeryl, isovaleryl and hexanoyl groups.

Where $R^{3a}$ represents a cycloalkylcarbonyl group, this has from 6 to 8 carbon atoms (i.e. from 5 to 7 carbon atoms in the cycloalkyl group). Examples of such groups include the cyclopentylcarbonyl, cyclohexylcarbonyl and cycloheptylcarbonyl groups.

Where $R^{3a}$ represents a heterocyclic acyl group, this is a group in which a heterocyclic group is attached to a carbonyl group. The heterocyclic part has from 4 to 7 ring atoms, more preferably 5 or 6 ring atoms, of which from 1 to 3, more preferably 1 or 2 and most preferably 1, are hetero-atoms selected from the group consisting of nitrogen, oxygen and sulfur atoms. Where there are 3 hetero-atoms in the heterocyclic group, these are preferably all nitrogen atoms or one or two are nitrogen atoms and, correspondingly, two or one are oxygen and/or sulfur atoms. The heterocyclic group is preferably aromatic. Examples of preferred heterocyclic acyl groups include the furoyl (more preferably 2-furoyl), thenoyl (more preferably 3-thenoyl), 3-pyridinecarbonyl (isonicotinoyl) and 4-pyridinecarbonyl(isonicotinoyl) groups.

Where $R^{3a}$ represents an alkoxycarbonyl group, this may be a straight or branched chain alkoxycarbonyl group having from 1 to 6 carbon atoms in the alkoxy part, i.e. having a total of from 2 to 7 carbon atoms, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl and hexyloxycarbonyl groups, of which we prefer those alkoxycarbonyl groups having from 2 to 4 carbon atoms and most prefer the ethoxycarbonyl group.

Where substituent χ represents an alkyl group, this may be a straight or branched chain alkyl group having from 1 to 4 carbon atoms, and examples are included among the alkyl groups exemplified in relation to $R^{1a}$ and $R^{2a}$.

Where substituent χ represents an alkoxy group, this may be a straight or branched chain alkoxy group having from 1 to 4 carbon atoms, and examples include the methoxy, ethoxy, propoxy, isopropoxy, butoxy, isobutoxy, sec-butoxy and t-butoxy groups, most preferably the methoxy group.

Where substituent χ represents a halogen atom, this may be, for example, a fluorine, chlorine, bromine or iodine atom.

Where substituent χ represents an alkylamino group having from 1 to 4 carbon atoms, this may be a straight or branched chain group, such as the methylamino, ethylamino, propylamino, isopropylamino, butylamino, isobutylamino, sec-butylamino or t-butylamino group, of which we prefer the methylamino group Where substituent χ represents a dialkylamino group having from 1 to 4 carbon atoms in each alkyl part, these may be straight or branched chain groups, such as the dimethylamino, diethylamino, dipropylamino, diisopropylamino, dibutylamino, diisobutylamino, di-sec-butylamino, di-t-butylamino, N-methyl-N-ethylamino, N-methyl-N-propylamino, N-methyl-N-isopropylamino, N-methyl-N-butylamino, N-methyl-N-isobutylamino, N-methyl-N-sec-butylamino, N-methyl-N-t-butylamino, N-ethyl-N-propylamino, N-ethyl-N-isopropylamino, N-ethyl-N-butylamino, N-ethyl-N-isobutylamino, N-ethyl-N-sec-butylamino, N-ethyl-N-t-butylamino, N-propyl-N-isopropylamino, N-propyl-N-butylamino, N-propyl-N-isobutylamino, N-propyl-N-sec-butylamino, N-propyl-N-t-butylamino, N-isopropyl-N-butylamino, N-isopropyl-N-isobutylamino, N-isopropyl-N-sec-butylamino, N-isopropyl-N-t-butylamino, N-butyl-N-isobutylamino, N-butyl-N-sec-butylamino, N-butyl-N-t-butylamino, N-isobutyl-N-sec-butylamino, N-isobutyl-N-t-butylamino and N-sec-butyl-N-t-butylamino groups, of which we prefer the dimethylamino group.

Where $R^{4a}$ or $R^{5a}$ represents an alkoxy group, this may be a straight or branched chain alkoxy group having from 1 to 5 carbon atoms, and examples include the methoxy, ethoxy, propoxy, isopropoxy, butoxy, isobutoxy, sec-butoxy, t-butoxy and pentyloxy groups, of which we prefer those alkoxy groups having from 1 to 4 carbon atoms and most prefer the methoxy group.

Where $R^{4a}$ and $R^{5a}$ together represent an alkylenedioxy group, this has from 1 to 4 carbon atoms and examples include the methylenedioxy, ethylenedioxy, propylenedioxy, trimethylenedioxy and tetramethylenedioxy groups, of which the methylenedioxy and ethylenedioxy groups are preferred.

Preferred examples of compounds of formula (I) include:
(2) Compounds in which $R^{1a}$ represents an alkyl group having from 1 to 4 carbon atoms.
(3) Compounds in which $R^{2a}$ represents a hydrogen atom or an alkyl group having from 1 to 3 carbon atoms.
(4) Compounds in which $R^{3a}$ represents a hydrogen atom, an aliphatic acyl group having from 1 to 4 carbon atoms, an unsubstituted benzoyl or naphthoyl group or an alkoxycarbonyl group having from 2 to 4 carbon atoms.
(5) Compounds in which $R^{4a}$ represents an alkyl group having from 1 to 4 carbon atoms.
(6) Compounds in which $R^{5a}$ represents a hydrogen atom or an alkyl group having from 1 to 3 carbon atoms.
(7) Compounds in which:
$R^{1a}$ represents an alkyl group having from 1 to 4 carbon atoms,
$R^{2a}$ represents a hydrogen atom or an alkyl group having from 1 to 3 carbon atoms,
$R^{3a}$ represents a hydrogen atom, an aliphatic acyl group having from 1 to 4 carbon atoms, an unsubstituted benzoyl or naphthoyl group or an alkoxycarbonyl group having from 2 to 4 carbon atoms,
$R^{4a}$ represents an alkyl group having from 1 to 4 carbon atoms, and
$R^{5a}$ represents a hydrogen atom or an alkyl group having from 1 to 3 carbon atoms.
(8) Compounds in which $R^{3a}$ represents a hydrogen atom, an acetyl group, a benzoyl group or an ethoxycarbonyl group.
(9) Compounds in which:
$R^{1a}$ represents an alkyl group having from 1 to 4 carbon atoms,
$R^{2a}$ represents a hydrogen atom or an alkyl group having from 1 to 3 carbon atoms,
$R^{3a}$ represents a hydrogen atom, an acetyl group, a benzoyl group or an ethoxycarbonyl group,
$R^{4a}$ represents an alkyl group having from 1 to 4 carbon atoms, and
$R^{5a}$ represents a hydrogen atom or an alkyl group having from 1 to 3 carbon atoms.
(10) Compounds in which $R^{1a}$ represents a methyl group.
(11) Compounds in which represents $R^{2a}$ hydrogen atom or a methyl group.
(12) Compounds in which $R^{3a}$ represents a hydrogen atom, an acetyl group or an ethoxycarbonyl group.
(13) Compounds in which $R^{4a}$ represents a methyl or t-butyl group.
(14) Compounds in which $R^{5a}$ represents a hydrogen atom or methyl group.
(15) Compounds in which:
$R^{1a}$ represents a methyl group,
$R^{2a}$ represents a hydrogen atom or a methyl group,
$R^{3a}$ represents a hydrogen atom, an acetyl group or an ethoxycarbonyl group,
$R^{4a}$ represents a methyl or t-butyl group, and
$R^{5a}$ represents a hydrogen atom or a methyl group.
(16) Compounds selected from:
i) 5-[4-(6-hydroxy-2,5,7,8-tetramethylchroman-2-ylmethoxy)benzyl]thiazolidine-2,4-dione (troglitazone),
ii) 5-[4-(6-hydroxy-2-methyl-7-t-butylchroman-2-ylmethoxy)benzyl]thiazolidine-2,4-dione,
iii) 5-[4-(6-hydroxy-2-ethyl-5,7,8-trimethylchroman-2-ylmethoxy)benzyl]thiazolidine- 2,4-dione,
iv) 5-[4-(6-hydroxy-2-isobutyl-5,7,8-trimethylchroman-2-ylmethoxy)benzyl]thiazolidine-2,4-dione, v) 5-[4-(6-acetoxy-2,5,7,8-tetramethylchroman-2-ylmethoxy)benzyl]thiazolidine-2,4-dione, and
vi) 5-[4-(6-ethoxycarbonyloxy-2,5,7,8-tetramethylchroman-2-ylmethoxy)benzyl]thiazolidine-2,4-dione.

(II) Japanese Patent Application Kokai No. Sho 61-267580 (Japanese Patent Publication No. Hei 5-66956) and U.S. Pat. No. 4,687,777 describe:
(1) thiazolidine derivatives of formula (II):

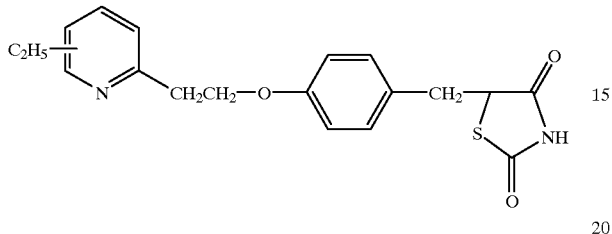

(II)

and pharmaceutically acceptable salts thereof.

In the compounds of formula (II), details, such as the kinds of pharmaceutically acceptable salt, the preparation process, examples of the compounds and preparative examples are described in Japanese Patent Application Kokai No. Sho 61-267580 (Japanese Patent Publication No. Hei 5-66956) and U.S. Pat. No. 4,687,777, the disclosures of which are incorporated herein by reference.

Preferred examples of the compounds of formula (II) include:
(2) Compounds selected from
i) 5-{4-[2-(3-ethyl-2-pyridyl)ethoxy]benzyl}thiazolidine-2,4-dione,
ii) 5-{4-[2-(4-ethyl-2-pyridyl)ethoxy]benzyl}thiazolidine-2,4-dione,
iii) 5-{([2-(5-ethyl-2-pyridyl)ethoxy]benzyl}thiazolidine-2,4-dione (which will hereinafter be called "pioglitazone") and
iv) 5-{4-[2-(6-ethyl-2-pyridyl)ethoxy]benzyl}thiazolidine-2,4-dione.

(III) Japanese Patent Application Kokai No. Sho 61-271287 (Japanese Patent Publication No. Hei 5-86953) and U.S. Pat. No. 4,703,052 describe:
(1) compounds of formula (III):

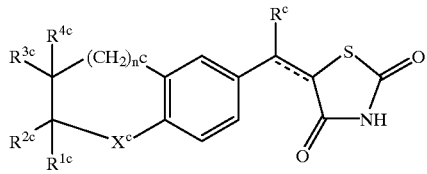

(III)

wherein:
==== represents a single or double bond;
$n^c$ represents 0, 1 or 2;
$X^c$ represents an oxygen atom, a sulfur atom, a sulfinyl group

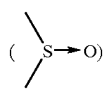

or a sulfonyl group

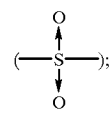

$R^c$ represents a hydrogen atom, a methyl group or an ethyl group;
$R^{1c}$ represents a cycloalkyl group having from 5 to 7 carbon atoms, a cycloalkyl group having from 5 to 7 carbon atoms and substituted by a methyl group, a pyridyl group, a thienyl group, a furyl group, a naphthyl group, a p-biphenylyl group, a tetrahydrofuranyl group, a tetrahydrothienyl group, a tetrahydropyranyl group, a group of formula $C_6H_4W^{2c}$
wherein $W^{2c}$ represents a hydrogen atom, a hydroxy group, a halogen atom (for example a fluorine, chlorine or bromine atom), an alkyl group having from 1 to 4 carbon atoms, an alkoxy group having from 1 to 4 carbon atoms or an alkylthio group having from 1 to 4 carbon atoms
or a group of formula alk-$W^{1c}$
wherein alk represents an alkylene group having from 1 to 6 carbon atoms, an ethylidene group or an isopropylidene group and $W^{1c}$ represents a hydrogen atom, a hydroxy group, an alkoxy group having from 1 to 4 carbon atoms, an alkylthio group having from 1 to 4 carbon atoms, a pyridyl group, a furyl group, a thienyl group, a tetrahydrofuryl group, a tetrahydrothienyl group, a naphthyl group, a cycloalkyl group having from 5 to 7 carbon atoms or a group of formula $C_6H_4W^{2c}$, where $W^{2c}$ is as defined above;
$R^{2c}$ represents a hydrogen atom or a methyl group;
$R^{3c}$ represents a hydrogen atom, an alkyl group having from 1 to 6 carbon atoms, a group of formula $C_6H_4W^{2c}$ where $W^{2c}$ is as defined above
or a benzyl group;
$R^{4c}$ represents a hydrogen atom, or
$R^{1c}$ and $R^{2c}$ together form an alkylene group having from 4 to 6 carbon atoms, and $R^{3c}$ and $R^{4c}$ both represent hydrogen atoms; or
$R^{3c}$ and $R^{4c}$ together form an alkylene group having from 4 to 6 carbon atoms, and $R^{1c}$ and $R^{2c}$ both represent hydrogen atoms; or
$R^{2c}$ and $R^{3c}$ together form an alkylene group having from 3 or 4 carbon atoms, and $R^{1c}$ and $R^{4c}$ both represent hydrogen atoms;
and pharmaceutically acceptable salts thereof.

In the compounds of formula (III), details, such as the definitions of $R^{1c}$, $R^{2c}$, $R^{3c}$, $W^{1c}$, $W^{2c}$ and alk, the kinds of pharmaceutically acceptable salt, the process for preparing the compounds of formula (III) and preparative examples are described in Japanese Patent Application Kokai No. Sho 61-271287 (Japanese Patent Publication No. Hei 5-86953) and U.S. Pat. No. 4,703,052, the disclosures of which are incorporated herein by reference.

For example, where $R^{1c}$ or $W^{1c}$ represents a cycloalkyl group, this may be a cyclopentyl, cyclohexyl or cycloheptyl group.

Where $W^{2c}$ represents an alkyl group or an alkoxy group or $W^{1c}$ represents an alkoxy group, this may be as defined and exemplified above in relation to substituents χ.

Where $W^{1c}$ or $W^{2c}$ represents an alkylthio group, this may be a straight or branched chain alkylthio group having from 1 to 4 carbon atoms, and examples include the methylthio, ethylthio, propylthio, isopropylthio, butylthio, isobutylthio, sec-butylthio and t-butylthio groups, most preferably the methylthio group.

Where alk represents an alkylene group having from 1 to 6 carbon atoms, this may be a straight or branched chain group having from 1 to 6 carbon atoms, and examples include the methylene, methylmethylene, ethylene, ethylidene, propylene, isopropylidene, propylidene, trimethylene, tetramethylene, 1-methyltrimethylene, 2-methyltrimethylene, 3-methyltrimethylene, pentamethylene, hexamethylene, 1,1-dimethyltrimethylene, 2,2-dimethyltrimethylene, 1,1-dimethyltetramethylene and 2,2-dimethyltetramethylene groups, of which we prefer the straight or branched chain alkylene groups having from 1 to 4 carbon atoms, more preferably the methylene or ethylene group.

Where $R^{3c}$ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups. Of these, we prefer those alkyl groups having from 1 to 4 carbon atoms, particularly the methyl, ethyl, propyl, isopropyl, butyl and isobutyl groups, and most preferably the methyl group.

Where $R^{1c}$ together with $R^{2c}$ or $R^{2c}$ together with $R^{3c}$ or $R^{3c}$ together with $R^{4c}$ represents an alkylene group having from 4 to 6 carbon atoms, this may be a straight or branched chain group, and examples include the tetramethylene, 1-methyltrimethylene, 2-methyltrimethylene, 3-methyltrimethylene, pentamethylene, hexamethylene, 1,1-dimethyltrimethylene, 2,2-dimethyltrimethylene, 1,1-dimethyltetramethylene and 2,2-dimethyltetramethylene groups.

Where $W^{1c}$ or $W^{2c}$ represents an alkoxy group having from 1 to 4 carbon atoms or where $W^{2c}$ represents a halogen atom or an alkyl group having from 1 to 4 carbon atoms, these may be as exemplified above in relation to substituent χ.

Preferred examples of the compounds of formula (III) include:
(2) The compound described in (1), wherein $R^c$ represents a hydrogen atom, ===represents a single bond and $n^c$ represents 0 or 1.
(3) The compound described in (2), wherein $R^{2c}$, $R^{3c}$ and $R^{4c}$ all represent hydrogen atoms, $R^{1c}$ represents a hydrogen atom, a cyclohexyl group, a group of formula $C_6H_4W^{2c}$ (wherein $W^{2c}$ represents a hydrogen atom, a fluorine atom, a chlorine atom, a bromine atom, a methyl group or a methoxy group) or a group of formula alk-$W^{1c}$ (wherein alk represents an alkylene group having from 1 to 4 carbon atoms, an ethylidene group or an isopropylidene group, and $W^{1c}$ represents a hydrogen atom, a hydroxy group, an alkoxy group having from 1 to 4 carbon atoms, a cyclohexyl group or a group of formula $C_6H_4W^{2c}$ where $W^{2c}$ is as defined above).
(4) The compound described in (3), wherein $X^c$ represents an oxygen atom, $R^{1c}$ represents a cyclohexyl group, a cyclohexylmethyl group, a benzyl group, a fluorobenzyl group, an alkyl group having from 1 to 4 carbon atoms, a hydroxymethyl group, a methoxymethyl group or an ethoxyethyl group.
(5) The compound described in (4), wherein $R^{1c}$ represents a benzyl group.
(6) The compound described in (5) which is 5-[(2-benzyl-2,3-dihydrobenzofuran-5-yl)methyl]thiazolidine-2,4-dione or 5-[(2-benzyl-3,4-dihydro-2H-benzopyran-6-yl)methyl]thiazolidine-2,4dione (englitazone) or a salt, preferably a sodium salt, thereof.
(7) The compound described in (2), wherein $R^{2c}$ and $R^{3c}$ together form a tetramethylene group, $R^{1c}$ and $R^{4c}$ each represents a hydrogen atom and $X^c$ represents an oxygen atom.
(8) The compound described in (2), wherein (a) $R^{1c}$ and $R^{2c}$ together form a pentamethylene group, $R^{3c}$ and $R^{4c}$ each represents a hydrogen atom and $X^c$ represents an oxygen atom; or (b) $R^{3c}$ and $R^{4c}$ together form a pentamethylene group, $R^{1c}$ and $R^{2c}$ each represents a hydrogen atom and $X^c$ represents an oxygen atom.
(9) The compound described in (3), wherein $n^c$ represents 0, $R^{1c}$ represents a hydrogen atom, a methyl group or a benzyl group and $X^c$ represents a sulfur atom or a sulfonyl group

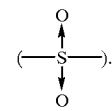

(IV) Japanese Patent Application Kokai Hei 1-131169 or U.S. Pat. Nos. 5,002,953, 5,194,443, 5,232,925 or 5,260,445 describe:
(1) compounds of formula (IV):

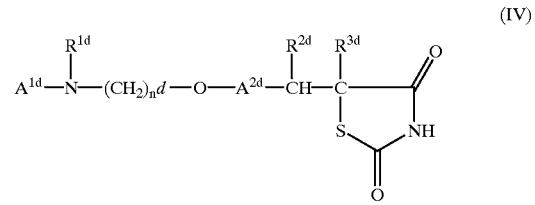

wherein:
$A^{1d}$ represents a substituted or unsubstituted aromatic heterocyclic group,
$R^{1d}$ represents a hydrogen atom, an alkyl group, an acyl group, an aralkyl group (the aryl moiety of said aralkyl group may be substituted or unsubstituted) or a substituted or unsubstituted aryl group,
$R^{2d}$ and $R^{3d}$ each represents a hydrogen atom or together form a bond,
$A^{2d}$ represents a benzene ring which has at most a total of 5 substituents; and
$n^d$ represents an integer of from 2 to 6;
and pharmaceutically acceptable salts thereof.

In the compounds of formula (IV), details, such as the definitions of $A^{1d}$, $R^{1d}$, $R^{2d}$, $R^{3d}$, $A^{2d}$ and $n^d$, the kinds of pharmaceutically acceptable salt, the process for preparing the compounds of formula (IV), preparative examples and preferred compounds are described in Japanese Patent Application Kokai Hei 1-131169 or U.S. Pat. Nos. 5,002,953, 5,194,443, 5,232,925 or 5,260,445, the disclosures of which are incorporated herein by reference.

For example, where $A^{1d}$ represents a substituted or unsubstituted aromatic heterocyclic group, this may be a single aromatic ring which has from 5 to 7 ring atoms, of which from 1 to 3 atoms are hetero-atoms selected from the group consisting of nitrogen, oxygen and sulfur atoms, or may be a fused ring system in which at least one of the rings is an aromatic heterocyclic group as defined above and the or each other ring is such an aromatic heterocyclic group or a carbocyclic aryl group. Where there are 3 hetero atoms in the aromatic heterocyclic group, these are preferably all nitrogen atoms or one or two are nitrogen atoms and, correspondingly, two or one are oxygen and/or sulfur atoms.

Examples of such single ring aromatic heterocyclic groups include the furyl, thienyl, pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyranyl, pyridyl, pyridazinyl, pyrimidinyl and pyrazinyl groups. Preferred groups are 5- to 7-membered aromatic heterocyclic groups which have at least one nitrogen atom and optionally one additional nitrogen, oxygen or sulfur atom. Examples of such groups include the pyrrolyl, azepinyl, pyrazolyl, imidazolyl, oxazolyl, isoxazolyl, thiazolyl, isothiazolyl, 1,2,3-oxadiazolyl, triazolyl, tetrazolyl, thiadiazolyl, pyridyl, pyridazinyl, pyrimidinyl and pyrazinyl groups. Of these, the pyridyl, imidazolyl, oxazolyl, pyrazinyl and thiazolyl groups are more preferred.

Various of the aromatic heterocyclic groups referred to above may form a fused ring with another cyclic group, and examples of such fused ring systems include the indolyl, benzofuryl, benzothienyl, benzoxazolyl, benzoimidazolyl, isoquinolyl, quinolyl and quinoxalyl groups.

These aromatic heterocyclic groups may be unsubstituted or they may be substituted by one or more substituents selected from the group consisting of substituents π defined exemplified below. There is no particular restriction on the number of substituents, except, such as may be imposed by the number of substitutable positions, and sometimes by steric constraints. However, in general, where the group is substituted, we prefer from 1 to 3 substituents.

Substituents π are selected from the group consisting of:
halogen atoms, such as fluorine, chlorine, bromine or iodine atoms;
alkyl groups having from 1 to 6 carbon atoms, such as those defined and exemplified above in relation to $R^{3c}$;
haloalkyl groups having from 1 to 6 carbon atoms, in which any of the alkyl groups defined and exemplified above in relation to $R^{3c}$ is substituted by one or more of the above halogen atoms, for example the fluoromethyl, chloromethyl, bromomethyl, iodomethyl, trifluoromethyl, trichloromethyl, 2-fluoroethyl, 2-chloroethyl, 2-bromoethyl, 2-iodoethyl, 2,2,2-trifluoroethyl, 2,2-difluoroethyl, 2,2, 2-trichloroethyl, 2,2-dichloroethyl, 2,2-dibromoethyl, 3-fluoropropyl, 4-chlorobutyl, 5-fluoropentyl and 6-fluorohexyl groups;
alkoxy groups having from 1 to 6 carbon atoms, which may be straight or branched chain groups having from 1 to 6, preferably from 1 to 4, carbon atoms, and examples include the methoxy, ethoxy, propoxy, isopropoxy, butoxy, isobutoxy, sec-butoxy, t-butoxy, pentyloxy, isopentyloxy, neopentyloxy, 2-methylbutoxy, 1-ethylpropoxy, hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, 1,2-dimethylbutoxy, 1,3-dimethylbutoxy, 2,3-dimethylbutoxy and 2-ethylbutoxy groups, of which we prefer those alkoxy groups having from 1 to 4 carbon atoms, particularly the methoxy, ethoxy, propoxy, isopropoxy, butoxy and isobutoxy groups, and most preferably the methoxy group;
aliphatic carboxylic acyl groups having from 1 to 6 carbon atoms, such as those defined and exemplified below in relation to $R^{1d}$;
alkanesulfonyl groups having from 1 to 6 carbon atoms, such as the methanesulfonyl, ethanesulfonyl, propanesulfonyl, isopropanesulfonyl, butanesulfonyl, isobutanesulfonyl, sec-butanesulfonyl, t-butanesulfonyl, pentanesulfonyl, isopentanesulfonyl, neopentanesulfonyl, 2-methylbutanesulfonyl, 1-ethylpropanesulfonyl, hexanesulfonyl, 4-methylpentanesulfonyl, 3-methylpentanesulfonyl, 2-methylpentanesulfonyl, 1-methylpentanesulfonyl, 3,3-dimethylbutanesulfonyl, 2,2-dimethylbutanesulfonyl, 1,1-dimethylbutanesulfonyl, 1,2-dimethylbutanesulfonyl, 1,3-dimethylbutanesulfonyl, 2,3-dimethylbutanesulfonyl and 2-ethylbutanesulfonyl groups;
haloalkanesulfonyl groups having from 1 to 6 carbon atoms, for example the fluoromethanesulfonyl, chloromethanesulfonyl, bromomethanesulfonyl, iodomethanesulfonyl, trifluoromethanesulfonyl, trichloromethanesulfonyl, 2-fluoroethanesulfonyl, 2-chloroethanesulfonyl, 2-bromoethanesulfonyl, 2-iodoethanesulfonyl, 2,2,2-trifluoroethanesulfonyl, 2,2-difluoroethanesulfonyl, 2,2,2-trichloroethanesulfonyl, 2,2-dichloroethanesulfonyl, 2,2-dibromoethanesulfonyl, 3-fluoropropanesulfonyl, 4-chlorobutanesulfonyl, 5-fluoropentanesulfonyl and 6-fluorohexanesulfonyl groups;
hydroxy groups, carboxy groups;
alkoxycarbonyl groups having from 1 to 6 carbon atoms in the alkoxy part, such as the methoxycarbonyl, ethoxycarbonyl, propoxycarbonyl, isopropoxycarbonyl, butoxycarbonyl, isobutoxycarbonyl, sec-butoxycarbonyl, t-butoxycarbonyl, pentyloxycarbonyl, isopentyloxycarbonyl, neopentyloxycarbonyl, 2-methylbutoxycarbonyl, 1-ethylpropoxycarbonyl, hexyloxycarbonyl, 4-methylpentyloxycarbonyl, 3-methylpentyloxycarbonyl, 2-methylpentyloxycarbonyl, 1-methylpentyloxycarbonyl, 3,3-dimethylbutoxycarbonyl, 2,2-dimethylbutoxycarbonyl, 1,1-dimethylbutoxycarbonyl, 1,2-dimethylbutoxycarbonyl, 1,3-dimethylbutoxycarbonyl, 2,3-dimethylbutoxycarbonyl and 2-ethylbutoxycarbonyl groups, of which we prefer those alkoxycarbonyl groups having from 2 to 5 carbon atoms, particularly the methoxycarbonyl, ethoxycarbonyl, propoxycarbonyl, isopropoxycarbonyl, butoxycarbonyl and isobutoxycarbonyl groups, and most preferably the methoxycarbonyl group;
acylamino groups having from 1 to 6 carbon atoms, in which the acyl part may be any of those acyl groups having from 1 to 6 carbon atoms included in the groups represented by $R^{1d}$;
alkanesulfonylamino groups having from 1 to 6 carbon atoms, in which the alkanesulfonyl part may be any of those alkanesulfonyl groups exemplified above;
haloalkanesulfonylamino groups having from 1 to 6 carbon atoms, in which the haloalkanesulfonyl part may be any of those haloalkanesulfonyl groups exemplified above;
amino groups, cyano groups, and
alkylenedioxy groups, such as those defined and exemplified above in relation to $R^{4a}$;

alkylene groups having from 1 to 8 carbon atoms (to form a cycloalkyl group fused with the aryl or heterocyclic ring) which may be any of the alkylene groups defined and exemplified above in relation to alk, and higher groups, such as the hexamethylene and octamethylene groups.

Where $R^{1d}$ represents an allyl group, this preferably has from 1 to 6 carbon atoms, and may be any one of those groups defined and exemplified above in relation to $R^{3c}$.

Where $R^{1d}$ represents an acyl group, this may be, for example:

an aliphatic acyl group, preferably: an alkanoyl group having from 1 to 25 carbon atoms, more preferably from 1 to 20 carbon atoms, still more preferably from 1 to 6 carbon atoms, and most preferably from 1 to 4 carbon atoms, (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred); a halogenated alkanoyl group having from 2 to 6 carbon atoms, especially a halogenated acetyl group (such as the chloroacetyl, dichloroacetyl, trichloroacetyl and trifluoroacetyl groups); a lower alkoxyalkanoyl group in which the alkoxy part has from 1 to 5, preferably from 1 to 3, carbon atoms and the alkanoyl part has from 2 to 6 carbon atoms and is preferably an acetyl group (such as the methoxyacetyl group); or an unsaturated analog of such a group, especially the alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

an aromatic acyl group, preferably an arylcarbonyl group, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents π, defined above, preferably: an unsubstituted group (such as the benzoyl, α-naphthoyl and β-naphthoyl groups); a halogenated arylcarbonyl group (such as the 2-bromobenzoyl and 4-chlorobenzoyl groups); a lower alkyl-substituted arylcarbonyl group, in which the or each alkyl substituent has from 1 to 5, preferably from 1 to 4, carbon atoms (such as the 2,4,6-trimethylbenzoyl and 4-toluoyl groups); a lower alkoxy-substituted arylcarbonyl group, in which the or each alkoxy substituent preferably has from 1 to 5, preferably from 1 to 4, carbon atoms (such as the 4-anisoyl group); a nitro-substituted arylcarbonyl group (such as the 4-nitrobenzoyl and 2-nitrobenzoyl groups); a lower alkoxycarbonyl-substituted arylcarbonyl group, in which the or each alkoxycarbonyl substituent preferably has from 2 to 6 carbon atoms [such as the 2-(methoxycarbonyl)benzoyl group]; or an aryl-substituted arylcarbonyl group, in which the aryl substituent is as defined above, except that, if it is substituted by a further aryl group, that aryl group is not itself substituted by an aryl group (such as the 4-phenylbenzoyl group);

an alkoxycarbonyl group, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

an alkenyloxycarbonyl group in which the alkenyl part has from 2 to 6, preferably from 2 to 4, carbon atoms (such as the vinyloxycarbonyl and allyloxycarbonyl groups); and an aralkyloxycarbonyl group, in which the aralkyl part is as defined and exemplified below, and in which the aryl ring, if substituted, preferably has one or two lower alkoxy or nitro substituents (such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups).

Where $R^{1d}$ represents an aralkyl group this is preferably a group in which an alkyl group having from 1 to 6 carbon atoms is substituted by at least one, and preferably from 1 to 3, aryl groups, which may themselves be substituted by one or more, preferably from 1 to 3 substituents selected from the group consisting of substituents π, defined above. Preferred examples of aralkyl groups include alkyl groups having from 1 to 4, more preferably from 1 to 3 and most preferably 1 or 2, carbon atoms which are substituted with from 1 to 3 aryl groups, which may be unsubstituted (such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, preferably a methylenedioxy group, [such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups].

Where $R^{1d}$ represents a substituted or unsubstituted aryl group, this is a carbocyclic aryl group having from 6 to 14, more preferably from 6 to 10, and most preferably 6 or 10, ring carbon atoms. The group may have a single aromatic ring or it may have two or more fused aromatic rings. The group may be unsubstituted or it may be substituted by one or more substituents selected from the group consisting of substituents π, defined above. There is no particular restriction on the number of substituents, except, such as may be imposed by the number of substitutable positions, and sometimes by steric constraints. However, in general, where the group is substituted, we prefer from 1 to 3 substituents. Examples of the unsubstituted groups include the phenyl, 1-naphthyl, 2-naphthyl, indenyl, phenanthrenyl and anthracenyl groups, of which the phenyl and naphthyl groups are preferred, the phenyl group being most preferred.

Examples of substituted groups include the 2-methoxyphenyl, 3-methoxyphenyl, 4-methoxyphenyl, 2,4-dimethoxyphenyl, 2,3-dimethoxyphenyl, 2,5-dimethoxyphenyl, 3,4-dimethoxyphenyl, 3,5-dimethoxyphenyl, 2,6-dimethoxyphenyl, 3,4,5-trimethoxyphenyl, 2,4,5-trimethoxyphenyl, 2,3,4-trimethoxyphenyl, 2,3,5-trimethoxyphenyl, 2,3,6-trimethoxyphenyl, 2,4,6-trimethoxyphenyl, 2-ethoxyphenyl, 3-ethoxyphenyl, 4-ethoxyphenyl, 2-isopropoxyphenyl, 3-isopropoxyphenyl, 4-isopropoxyphenyl, 2-methylphenyl, 3-methylphenyl, 4-methylphenyl, 2,4-dimethylphenyl, 2,3-dimethylphenyl, 2,5-dimethylphenyl, 3,4-dimethylphenyl, 3,5-dimethylphenyl, 2,6-dimethylphenyl, 3,4,5- trimethylphenyl, 2,4,5-trimethylphenyl, 2,3,4-trimethylphenyl, 2,3,5-trimethylphenyl, 2,3,6-trimethylphenyl, 2,4,6-trimethylphenyl, 2-chlorophenyl, 3-chlorophenyl, 4-chlorophenyl, 2,4-dichlorophenyl, 2,3-dichlorophenyl, 2,5-dichlorophenyl, 3,4-dichlorophenyl, 3,5-dichlorophenyl, 2,6-dichlorophenyl, 3,4,5-trichlorophenyl, 2,4,5-trichlorophenyl, 2,3,4-trichlorophenyl, 2,3,5-trichlorophenyl, 2,3,6-trichlorophenyl, 2,4,6-trichlorophenyl, 2-fluorophenyl, 3-fluorophenyl, 4-fluorophenyl, 2,4-difluorophenyl, 2,3-difluorophenyl, 3,4-difluorophenyl, 3,5-difluorophenyl, 2,6-difluorophenyl, 3,4,5-trifluorophenyl, 2,4,5-trifluorophenyl, 2-trifluoromethylphenyl, 3-trifluoromethylphenyl, 4-trifluoromethylphenyl, 2,4-bis(trifluoromethyl)phenyl, 2,3-bis(trifluoromethyl)phenyl, 3,4-bis(trifluoromethyl)phenyl, 3,5-bis(trifluoromethyl)phenyl, 2,6-bis(trifluoromethyl)phenyl, 3,4,5-tris(trifluoromethyl)phenyl, 2,4,5-tris-(trifluoromethyl)phenyl, 2-acetamidophenyl, 3-acetamidophenyl, 4-acetamidophenyl, 2-methoxycarbonylphenyl, 3-methoxycarbonylphenyl, and 4-methoxycarbonylphenyl groups.

Where $A^{2d}$ represents a benzene ring which has at most a total of 5 substituents, these are preferably selected from the group consisting of substituents π, defined above.

Preferred examples of compounds of formula (IV) include:

(2) The compounds described in (1), wherein $A^{1d}$ represents a substituted or unsubstituted, single ring or fused ring aromatic heterocylic group which has 4 or less heteroatoms selected from oxygen, sulfur and nitrogen atoms.

(3) The compounds described in (1) or (2), wherein $A^{1d}$ represents a group of formula (a), (b) or (c):

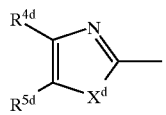

(a)

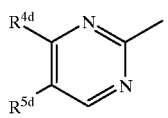

(b)

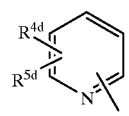

(c)

wherein $R^{4d}$ and $R^{5d}$ each independently represents a hydrogen atoms, an alkyl group or a substituted or unsubstituted aryl group; or $R^{4d}$ and $R^{5d}$, together with carbon atoms to which they are attached, form a benzene ring and each of the carbon atoms of the benzene ring may be substituted or unsubstituted; and, in the group of formula (a), $X^d$ represents an oxygen or sulfur atoms.

(4) The compounds described in (3), wherein $R^{4d}$ and $R^{5d}$ each independently represents a hydrogen atom, an alkyl group or substituted or unsubstituted phenyl group.

(5) The compounds described in (3), wherein $R^{4d}$ and $R^{5d}$ together form a group of formula d:

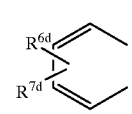

(d)

wherein $R^{6d}$ and $R^{7d}$ each independently represents a hydrogen atom, a halogen atom, a substituted or unsubstituted alkyl group or an alkoxy group.

(6) The compounds described in (5), wherein $R^{6d}$ and $R^{7d}$ each represents a hydrogen atom.

(7) The compounds described in any one of (1) to (6), wherein $A^{2d}$ represents a group of formula (e):

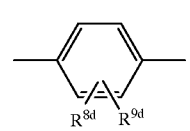

(e)

wherein $R^{8d}$ and $R^{9d}$ each independently represents a hydrogen atom, a halogen atom, a substituted or unsubstituted alkyl group of an alkoxy group.

(8) The compounds described in (7), wherein $R^{8d}$ and $R^{9d}$ each represents a hydrogen atom.

(9) The compounds described in (1) which are of formula (f):

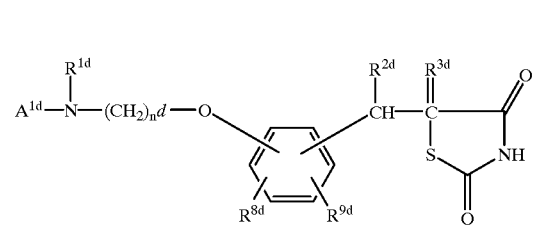

(f)

wherein $A^{1d}$, $R^{1d}$, $R^{2d}$, $R^{3d}$ and $n^d$ are as defined in formula (IV) or (1) and $R^{8d}$ and $R^{9d}$ are as defined in the formula (e) of (7)] and pharmaceutically acceptable salts thereof.

(10) The compounds described in any one of (1) to (9), wherein $n^d$ represents an integer of 2 or 3.

(11) The compounds described in any one of (1) to (10), wherein $R^{1d}$ represents a methyl group.

(12) The compounds described in (1) which are selected from:

i) 5-(4-{2-[N-methyl-N-(2-benzothiazolyl)amino]ethoxy}benzyl)thiazolidine-2,4-dione, ii) 5-(4-{2-[N-methyl-N-(2-pyrimidinyl)amino]ethoxy}benzyl)thiazolidine-2,4-dione, iii) 5-(4-{2-[N-methyl-N-(4,5-dimethylthiazol-2-yl)amino]ethoxy}benzyl)thiazolidine-2,4-dione, iv) 5-{4-[2-(N-methyl-N-thiazol-2-ylamino)ethoxy]benzyl}thiazolidine-2,4-dione, v) 5-(4-{2-[N-methyl-N-(4-phenylthiazol-2-yl)amino]ethoxy}benzyl)thiazolidine-2,4-dione, vi) 5-(4-{2-[N-methyl-N-(4-phenyl-5-methylthiazol-2-yl)amino]ethoxy}benzyl)thiazolidine-2,4-dione, vii) 5-(4-{2-[N-methyl-N-(4-methyl-5-phenylthiazol-2-yl)amino]ethoxy}benzyl)thiazolidine-2,4-dione, viii) 5-(4-{2-[N-methyl-N-(5-phenyloxazol-2-yl)amino]ethoxy}benzyl)thiazolidine-2,4-dione, ix) 5-(4-{2-[N-methyl-N-(4,5-dimethyloxazol-2-yl)amino]ethoxy}benzyl)thiazolidine-2,4-dione, x) 5-{4-[2-(2-pyrimidinylamino)ethoxy]benzyl}thiazolidine-2,4-dione, xi) 5-{4-[2-(N-acetyl-N-pyrimidin-2-ylamino)ethoxy]benzyl}thiazolidine-2,4-dione, xii) 5-{4-[2-(N-benzothiazol-2-yl-N-benzylamino)ethoxy]benzyl}thiazolidine-2,4-dione, xiii) 5-{4-[3-(N-methyl-N-benzoxazol-2-ylamnino)propoxy]benzyl}thiazolidine-2,4-dione, and xiv) 5-{4-[2-(N-methyl-N-pyrid-2-ylamino)ethoxy]benzyl}thiazolidine-2,4-dione (which will hereinafter be called "rosiglitazone").

(13) The compound described in (1) which is 5-{4-[2-(N-methyl-N-pyrid-2-ylamino)ethoxy]benzyl}thiazolidine-2,4-dione (rosiglitazone).

In (2) to (11), details of the definitions of $R^{4d}$, $R^{5d}$, $R^{6d}$, $R^{7d}$, $R^{8d}$ and $R^{9d}$ are described in Japanese Patent Application Kokai Hei 1-131169 or U.S. Pat. Nos. 5,002,953, 5,194,443, 5,232,925 or 5,260,445, the disclosures of which are incorporated herein by reference.

(V) Japanese Patent Application Kokai No. Hei 9-48779 and European Patent Publication No. 708098A describe:

(1) oxime derivatives of formula (V):

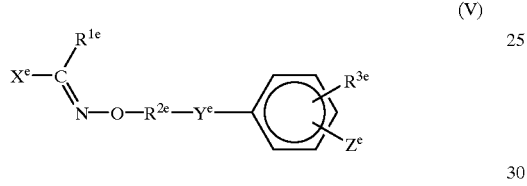

and pharmaceutically acceptable salts thereof;
wherein:

$R^{1e}$ represents a hydrogen atom or a straight or branched chain alkyl group having from 1 to 6 carbon atoms, $R^{2e}$ represents a straight or branched chain alkylene group having from 2 to 6 carbon atoms, $R^{3e}$ represents a hydrogen atom, a straight or branched chain alkyl group having from 1 to 6 carbon atoms, a straight or branched chain alkoxy group having from 1 to 4 carbon atoms, a straight or branched chain alkylthio group having from 1 to 4 carbon atoms, a halogen atom, a nitro group, an amino group, a straight or branched chain monoalkylamino group having from 1 to 4 carbon atoms, a straight or branched chain dialkylamino group in which each alkyl group has from 1 to 4 carbon atoms, an aryl group having from 6 to 10 carbon atoms or an aralkyl group having from 7 to 12 carbon atoms, $X^e$ represents an aryl group having from 6 to 10 carbon atoms which is unsubstituted or is substituted by from 1 to 3 of substituents α, defined below, or a heteroaromatic group which is unsubstituted or is substituted by from 1 to 3 of substituents α, defined below, said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain acyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a halogen atom, (xi) a nitro group, (xii) an amino group, (xiii) a straight or branched chain monoalkylamino group having from 1 to 4 carbon atoms, (xiv) a straight or branched chain dialkylamino group in which each alkyl group has from 1 to 4 carbon atoms, (xv) an aralkyl group having from 7 to 12 carbon atoms, (xvi) an aryl group having from 6 to 10 carbon atoms which is unsubstituted or is substituted by at least one substituent selected from the group consisting of substituents β, defined below, (xvii) an aryloxy group having from 6 to 10 carbon atoms which is unsubstituted or is substituted by at least one substituent selected from the group consisting of substituents β, defined below, (xviii) an arylthio group having from 6 to 10 carbon atoms which is unsubstituted or is substituted by at least one substituent selected from the group consisting of substituents β, defined below, (xix) an arylsulfonyl group having from 6 to 10 carbon atoms which is unsubstituted or is substituted by at least one substituent selected from the group consisting of substituents β, defined below, (xx) an arylsulfonylamino group having from 6 to 10 carbon atoms which is unsubstituted or is substituted by at least one substituent selected from the group consisting of substituents β, defined below, and in which the nitrogen atom of the amino moiety is unsubstituted or is substituted by a straight or branched chain alkyl group having from 1 to 6 carbon atoms, (xxi) a heteroaromatic group, (xxii) a heteroaryloxy group, (xxiii) a heteroarylthio group, (xxiv) a heteroarylsulfonyl group or (xxv) a heteroaromatic sulfonylamino group in which the nitrogen atom of the amino moiety is unsubstituted or is substituted by a straight or branched chain alkyl group having from 1 to 6 carbon atoms;

said substituent β representing a straight or branched chain alkyl group having from 1 to 6 carbon atoms, a straight or branched chain haloalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms;

$Y^e$ represents an oxygen atom, a sulfur atom or group of formula >N-$R^{4e}$ (wherein $R^{4e}$ represents a hydrogen atom, a straight or branched chain alkyl group having from 1 to 6 carbon atoms or a straight or branched chain acyl group having from 1 to 8 carbon atoms); and $Z^e$ represents a 2,4-dioxothiazolidin-5-ylidenylmethyl, 2,4-dioxothiazolidin-5-ylmethyl, 2,4-dioxooxazolidin-5-ylmethyl or 3,5-dioxooxadiazolidin-2-ylmethyl group.

In the compounds of formula (V), details, such as the definitions of $R^{1e}$, $R^{2e}$, $R^{3e}$, $R^{4e}$, α, β, $X^e$, $Y^e$ and $Z^e$, the kinds of pharmaceutically acceptable salt, the process for preparing the compounds of formula (V), examples of the compounds and preparative examples are described in Japanese Patent Application Kokai No. Hei 9-48779 and European Patent Publication No. 708098A, the disclosures of which are incorporated herein by reference.

For example, where $R^{3e}$, substituent α or substituent β represents an alkoxy group having from 1 to 4 carbon atoms or a halogen atom, or where $R^{3e}$ or substituent α represents a mono- or di- alkylamino group, these may be as defined and exemplified above in relation to substituent χ.

Where $R^{3e}$, substituent α or substituent β represents an alkylenedioxy group, this may be as defined and exemplified above in relation to $R^{4a}$ and $R^{5a}$.

Where $R^{3e}$ or substituent α represents an alkylthio group, this may be as defined and exemplified above in relation to $W^{2c}$.

Where $R^{3e}$, substituent α, substituent β or $R^{4e}$ represents an alkyl group having from 1 to 6 carbon atoms, this may be as defined and exemplified above in relation to $R^{3c}$.

Where $X^e$ or substituent α represents a heteroaromatic group, this may be as defined and exemplified above for the heterocyclic aromatic groups in relation to $A^{1d}$.

Where $R^{3e}$ or substituent α represents an aralkyl group, or $R^{3e}$, $X^e$ or substituent α represents an aryl group, these may be as defined and exemplified above in relation to $R^{1d}$.

Where $R^{2e}$ represents a straight or branched chain alkylene group having from 2 to 6 carbon atoms, this may be selected from the alkylene groups defined and exemplified above in relation to alk.

Where substituent α or substituent β represents a haloalkyl group, the alkyl part may be a straight or branched chain group having from 1 to 6, preferably from 1 to 3, carbon atoms. There is no restriction on the number of halogen atoms, except that imposed by the number of substitutable positions; however, in general, from 1 to 3 halogen atoms are preferred. Examples of such groups include the trifluoromethyl, trichloromethyl, difluoromethyl, dichloromethyl, dibromomethyl, fluoromethyl, chloromethyl, bromomethyl, iodomethyl, 2,2,2-trichloroethyl, 2,2,2-trifluoroethyl, 2-bromoethyl, 2-chloroethyl, 2-fluoroethyl, 2-iodoethyl, 2,2-dibromoethyl, 3-brompropyl, 3-chloropropyl, 3-fluoropropyl, 3-iodopropyl, 4-bromobutyl, 4-chlorobutyl, 4-fluorobutyl, 4-iodobutyl, 5-bromopentyl, 5-chloropentyl, 5-fluoropentyl, 5-iodopentyl, 6-bromohexyl, 6-chlorohexyl, 6-fluorohexyl and 6-iodohexyl groups, of which we prefer the trifluoromethyl, 2-bromoethyl, 2-chloroethyl and 2-fluoroethyl groups.

Where substituent α represents an acyloxy group, this has from 1 to 4 carbon atoms and may be a straight or branched chain aliphatic group. Examples of such groups include the formyloxy, acetoxy, propionyloxy, butyryloxy and isobutyryloxy groups.

Where substituent α represents an aralkyloxy, aryloxy, arylthio, arylsulfonyl, arylsulfonylamino, heteroaryloxy, heteroarylthio, heteroarylsulfonyl or heteroarylsulfonylamino group, the aralkyl, aryl or heteroaryl part may be as defined and exemplified above.

Where substituent α represents an acyl group having from 1 to 8 carbon atoms, this is preferably an aliphatic or carbocyclic aromatic group, and examples include:

aliphatic acyl groups, preferably: alkanoyl groups having from 1 to 8 carbon atoms, more preferably from 1 to 6 carbon atoms, and most preferably from 1 to 4 carbon atoms, such as the formyl, acetyl, propionyl, butyryl, isobutyryl, pivaloyl, valeryl, isovaleryl, hexanoyl, heptanoyl and octanoyl groups, of which the acetyl group is most preferred; halogenated alkanoyl groups having from 2 to 6 carbon atoms, especially halogenated acetyl groups, such as the chloroacetyl, dichloroacetyl, trichloroacetyl and trifluoroacetyl groups; lower alkoxyalkanoyl groups in which the alkoxy part has from 1 to 5, preferably from 1 to 3, carbon atoms and the alkanoyl part has from 2 to 6 carbon atoms and is preferably an acetyl group, such as the methoxyacetyl group; and unsaturated analogs of such groups, especially alkenoyl or alkynoyl groups having from 3 to 6 carbon atoms, such as the acryloyl, methacryloyl, propioloyl, crotonoyl, isocrotonoyl and (E)-2-methyl-2-butenoyl groups; and aromatic acyl groups, preferably arylcarbonyl groups, such as the benzoyl, α-naphthoyl and β-naphthoyl groups; halogenated arylcarbonyl groups, such as the 2-bromobenzoyl and 4-chlorobenzoyl groups; lower alkyl-substituted arylcarbonyl groups, such as the 4-toluoyl group; lower alkoxy-substituted arylcarbonyl groups, such as the 4-anisoyl group; nitro-substituted arylcarbonyl groups, such as the 4-nitrobenzoyl and 2-nitrobenzoyl groups; and lower alkoxycarbonyl-substituted arylcarbonyl groups, such as the 2-(methoxycarbonyl)benzoyl group.

Preferred examples of compounds of formula (V) include:
(2) The compounds described in (1), wherein $R^{1e}$ represents a hydrogen atom or a straight or branched chain alkyl group having from 1 to 4 carbon atoms.
(3) The compounds described in (1), wherein $R^{1e}$ represents a hydrogen atom or a straight or branched chain alkyl group having from 1 to 3 carbon atoms.
(4) The compounds described in (1), wherein $R^{1e}$ represents a hydrogen atom, a methyl group or an ethyl group.
(5) The compounds described in (1), wherein $R^{1e}$ represents a methyl or ethyl group.
(6) The compounds described in (1), wherein $R^{2e}$ represents a straight or branched chain alkylene group having from 2 to 5 carbon atoms.
(7) The compounds described in (1), wherein $R^{2e}$ represents a straight or branched chain alkylene group having 2 or 3 carbon atoms.
(8) The compounds described in (1), wherein $R^{2e}$ represents an ethylene, trimethylene or methylethylene group.
(9) The compounds described in (1), wherein $R^{2e}$ represents an ethylene group.
(10) The compounds described in (1), wherein $R^{3e}$ represents a hydrogen atom, a straight or branched chain alkyl group having from 1 to 4 carbon atoms, a methoxy group, an ethoxy group, a methylthio group, an ethylthio group or a halogen atom.
(11) The compounds described in (1), wherein $R^{3e}$ represents a hydrogen atom.
(12) The compounds described in (1), wherein $X^e$ represents an aryl group having from 6 to 10 carbon atoms which is unsubstituted or is substituted by from 1 to 3 substituents selected from the group consisting of substituents α or a heteroaromatic group which has from 5 to 10 ring atoms (and which may have one or two rings) of which from 1 to 3 are hetero-atoms selected from the group consisting of nitrogen, oxygen and sulfur atoms and which is unsubstituted or is substituted by from 1 to 3 substituents selected from the group consisting of substituents α,
said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain acyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a halogen atom, (xi) an aralkyl group having from 7 to 12 carbon atoms, (xii) a phenyl group which is unsubstituted or is substituted by at least one substituent selected from the group consisting of substituents β, (xiii) a phenoxy group which is unsubstituted or is substituted by at least one substituent selected from the group consisting of substituents β, (xiv) a phenylthio group which is unsubstituted or is substituted by at least one substituent selected from the group consisting of substituents β, (xv) a phenylsulfonyl group which is unsubstituted or is substituted by at least one substituent selected from the group consisting of substituents β, (xvi) a phenylsulfonylamino group which is unsubstituted or is substituted by at least one substituent selected from the group consisting of substituents β and in which the nitrogen atom of the amino moiety is unsubstituted or is substituted by a straight or branched chain alkyl group having from 1 to 6 carbon atoms, (xvii) a furyl, thienyl, oxazolyl, isoxazolyl, thiazolyl, pyridyl, pyridyloxy, pyridylthio or pyridylsulfonyl group, (xviii) an imidazolyl group in which the nitrogen atom is unsubstituted or is substituted by a straight or branched chain alkyl group having from 1 to 6 carbon atoms and/or (xix) a pyridylsulfonylamino group in which the nitrogen atom of the amino moiety is unsubstituted or is substituted by a straight or branched chain alkyl group having from 1 to 6 carbon atoms; and said substituent β representing a straight or branched chain alkyl group having from 1 to 6 carbon atoms, a straight or branched chain haloalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms.

(13) The compounds described in (1), wherein $X^e$ represents an aryl group having from 6 to 10 carbon atoms which is unsubstituted or is substituted by from 1 to 3 substituents selected from the group consisting of substituents α or a heteroaromatic group which has from 5 to 10 ring atoms (and which may have one or two rings) of which from 1 to 3 are hetero-atoms selected from the group consisting of nitrogen, oxygen and sulfur atoms and which is unsubstituted or is substituted by from 1 to 3 substituents selected from the group consisting of substituents α, said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a fluorine, chlorine or bromine atom, (xi) an aralkyl group having from 7 to 12 carbon atoms, (xii) a phenyl group which is unsubstituted or is substituted by at least one substituent selected from the group consisting of substituents β, (xiii) a phenoxy group which is unsubstituted or is substituted by at least one substituent selected from the group consisting of substituents β, (xiv) a phenylthio group which is unsubstituted or is substituted by at least one substituent selected from the group consisting of substituents β, (xv) a phenylsulfonyl group which is unsubstituted or is substituted by at least one substituent selected from the group consisting of substituents β, (xvi) a phenylsulfonylamino group which is unsubstituted or is substituted by at least one substituent selected from the group consisting of substituents β and in which the nitrogen atom of the amino moiety is unsubstituted or is substituted by a straight or branched chain alkyl group having from 1 to 6 carbon atoms, (xvii) a furyl, thienyl, oxazolyl, isoxazolyl, thiazolyl, pyridyl, pyridyloxy, pyridylthio or pyridylsulfonyl group, (xviii) an imidazolyl group in which the nitrogen atom is unsubstituted or is substituted by a straight or branched chain alkyl group having from 1 to 6 carbon atoms) and/or (xix) a pyridylsulfonylamino group in which the nitrogen atom of the amino moiety is unsubstituted or is substituted by a straight or branched chain alkyl group having from 1 to 6 carbon atoms; and said substituent β representing a straight or branched chain alkyl group having from 1 to 6 carbon atoms, a straight or branched chain haloalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms.

(14) The compounds described in (1), wherein $X^e$ represents a phenyl, naphthyl, imidazolyl, oxazolyl, pyridyl, indolyl, quinolyl or isoquinolyl group which is unsubstituted or is substituted by from 1 to 3 substituents selected from the group consisting of substituents α, said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy group, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a fluorine, chlorine or bromine atom, (xi) an aralkyl group having from 7 to 12 carbon atoms, (xii) a phenyl group which is unsubstituted or is substituted by at least one substituent selected from the group consisting of methyl, trifluoromethyl, methoxy, fluoro and methylenedioxy groups, (xiii) a phenoxy group which is unsubstituted or is substituted by at least one substituent selected from the group consisting of methyl, trifluoromethyl, methoxy, fluoro and methylenedioxy groups, (xiv) a phenylthio group which is unsubstituted or is substituted by at least one substituent selected from the group consisting of methyl, trifluoromethyl, methoxy, fluoro and methylenedioxy groups, (xv) a phenylsulfonyl group which is unsubstituted or is substituted by at least one substituent selected from the group consisting of methyl, trifluoromethyl, methoxy, fluoro and methylenedioxy groups, (xvi) a phenylsulfonylamino group which is unsubstituted or is substituted by at least one substituent selected from the group consisting of methyl, trifluoromethyl, methoxy, fluoro and methylenedioxy groups and in which the nitrogen atom of the amino moiety is unsubstituted or is substituted by at least one substituent selected from the group consisting of straight or branched chain alkyl groups having from 1 to 6 carbon atoms, (xvii) a furyl, thienyl, oxazolyl, isoxazolyl, thiazolyl, pyridyl, pyridyloxy, pyridylthio or pyridylsulfonyl group, (xviii) an imidazolyl group in which the nitrogen atom is unsubstituted or is substituted by a straight or branched chain alkyl group having from 1 to 6 carbon atoms or (xix) a pyridylsulfonylamino group in which the nitrogen atom of the amino moiety is unsubstituted or is substituted by a straight or branched chain alkyl group having from 1 to 6 carbon atoms.

(15) The compounds described in (1), wherein $X^e$ represents a phenyl, naphthyl, imidazolyl, oxazolyl, pyridyl, indolyl, quinolyl or isoquinolyl group which is unsubstituted or is substituted by from 1 to 3 substituents selected from the group consisting of substituents α, said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy, benzyloxy, phenethyloxy or naphthylmethoxy group, (vii) a straight or branched chain alkylthio group having from 1 to 4 carbon atoms, (viii) a straight or branched chain alkylsulfonyl group having from 1 to 4 carbon atoms, (ix) a fluorine, chlorine or bromine atom, (x) a benzyl group, (xi) a phenyl group which is unsubstituted or is substituted by at least one substituent selected from the group consisting of methyl, trifluoromethyl, methoxy, fluoro and methylenedioxy groups, (xii) a phenoxy group which is unsubstituted or is substituted by at least one substituent selected from the group consisting of methyl, trifluoromethyl, methoxy, fluoro and methylenedioxy groups, (xiii) a phenylthio, phenylsulfonyl, phenylsulfonylamino, N-methylphenylsulfonylamino, furyl, thienyl, oxazolyl, isoxazolyl, thiazolyl, pyridyl, pyridyloxy, pyridylthio, pyridylsulfonyl, pyridylsulfonylamino or N-methylpyridylsulfonylamino group and/or (xiv) an imidazolyl group in which the nitrogen atom is unsubstituted or is substituted by a straight or branched chain alkyl group having from 1 to 6 carbon atoms.

(16) The compounds described in (1), wherein $X^e$ represents a phenyl, naphthyl, pyridyl, indolyl, quinolyl or isoquinolyl group which is unsubstituted or is substituted by from 1 to 3 substituents selected from the group consisting of substituents α, said substituents α each representing (i) a straight or branched chain alkyl group having from 1 to 3 carbon atoms, (ii) a trifluoromethyl, difluoromethyl, fluoromethyl, hydroxy, formyloxy or acetoxy group, (iii) a straight or branched chain alkoxy group having from 1 to 3 carbon atoms, (iv) a methylenedioxy, benzyloxy, methylthio, ethylthio, methylsulfonyl or ethylsulfonyl group, (v) a fluorine, chlorine or bromine atom, (vi) a benzyl, phenyl, 4-methylphenyl, 4-trifluoromethylphenyl, 4-methoxyphenyl, 4-fluorophenyl, 3,4-methylenedioxyphenyl, phenoxy, phenylthio, phenylsulfonyl, phenylsulfonylamino, N-methylphenylsulfonylamino, furyl, thienyl, oxazolyl, thiazolyl, imidazolyl, N-methylimidazolyl, pyridyl, pyridyloxy, pyridylthio, pyridylsulfonyl, pyridylsulfonylamino and/or N-methylpyridylsulfonylamino group.

(17) The compounds described in (1), wherein $X^e$ represents a phenyl, naphthyl, pyridyl, quinolyl or isoquinolyl group which is unsubstituted or is substituted by from 1 to 3 substituents selected from the group consisting of substituents α, said substituents α each representing a methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl, chlorine, benzyl, phenyl, phenoxy, phenylthio, phenylsulfonyl, phenylsulfonylamino, N-methylphenylsulfonylamino, pyridyl, pyridyloxy, pyridylthio, pyridylsulfonyl, pyridylsulfonylamino and/or N-methylpyridylsulfonylamino group.

(18) The compounds described in (1), wherein $X^e$ represents a phenyl group which is unsubstituted or is substituted by from 1 to 3 substituents selected from the group consisting of substituents α, said substituents α each representing a methyl, hydroxy, acetoxy, chlorine, benzyl, phenyl, phenoxy, phenylthio, phenylsulfonyl, phenylsulfonylamino, N-methylphenylsulfonylamino, pyridyl, pyridyloxy, pyridylthio and/or pyridylsulfonyl group.

(19) The compounds described in (1), wherein $X^e$ represents a pyridyl group which is unsubstituted or is substituted by from 1 to 3 substituents selected from the group consisting of substituents α, said substituents α each representing a methoxy, ethoxy, isopropoxy, benzyloxy, methylthio, ethylthio, methylsulfonyl, ethylsulfonyl, benzyl, phenyl, phenoxy, phenylthio, phenylsulfonyl, phenylsulfonylamino and/or N-methylphenylsulfonylamino group.

(20) The compounds described in (1), wherein $Y^e$ represents an oxygen atom, a sulfur atom or a group of formula $>N-R^{4e}$ (wherein $R^{4e}$ represents a hydrogen atom, a straight or branched chain alkyl group having from 1 to 3 carbon atoms or a straight or branched chain alkanoyl group having from 2 to 5 carbon atoms).

(21) The compounds described in (1), wherein $Y^e$ represents an oxygen atom.

(22) The compounds described in (1), wherein $Z^e$ represents a 2,4-dioxothiazolidin-5-ylmethyl, 2,4-dioxooxazolidin-5-ylmethyl or 3,5-dioxooxadiazolidin-2-ylmethyl group.

(23) The compounds described in (1), wherein $Z^e$ represents a 2,4-dioxothiazolidin-5-ylmethyl or 2,4-dioxooxazolidin-5-ylmethyl group.

(24) The compounds described in (1), wherein $Z^e$ represents a 2,4-dioxothiazolidin-5-ylmethyl group.

(25) The compounds described in (1), wherein $R^{1e}$ represents a hydrogen atom or a straight or branched chain alkyl group having from 1 to 4 carbon atoms, $R^{2e}$ represents a straight or branched chain alkylene group having from 2 to 5 carbon atoms, $R^{3e}$ represents a hydrogen atom, a straight or branched chain alkyl group having from 1 to 4 carbon atoms, a methoxy group, an ethoxy group, a methylthio group, an ethylthio group or a halogen atom, $X^e$ represents an aryl group having from 6 to 10 carbon atoms which is unsubstituted or is substituted by from 1 to 3 substituents selected from the group consisting of substituents α or a heteroaromatic group which has from 5 to 10 ring atoms (and which may have one or two rings) of which from 1 to 3 are hetero-atoms selected from the group consisting of nitrogen, oxygen and sulfur atoms and which is unsubstituted or is substituted by from 1 to 3 substituents selected from the group consisting of substituents α, said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain acyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a halogen atom, (xi) an aralkyl group having from 7 to 12 carbon atoms, (xii) a phenyl group which is unsubstituted or is substituted by at least one substituent selected from the group consisting of substituents β, (xiii) a phenoxy group which is unsubstituted or is substituted by at least one substituent selected from the group consisting of substituents β, (xiv) a phenylthio group which is unsubstituted or is substituted by at least one substituent selected from the group consisting of substituents β, (xv) a phenylsulfonyl group which is unsubstituted or is substituted by at least one substituent selected from the group consisting of substituents β, (xvi) a phenylsulfonylamino group which is unsubstituted or is substituted by at least one substituent selected from the group consisting of substituents β and in which the nitrogen atom of the amino moiety is unsubstituted or is substituted by a straight or branched chain alkyl group having from 1 to 6 carbon atoms, (xvii) a furyl, thienyl, oxazolyl, isoxazolyl, thiazolyl, pyridyl, pyridyloxy, pyridylthio or pyridylsulfonyl group, (xviii) an imidazolyl group in which the nitrogen atom is unsubstituted or is substituted by a straight or branched chain alkyl group having from 1 to 6 carbon atoms and/or (xix) a pyridylsulfonylamino group in which the nitrogen atom of the amino moiety is unsubstituted or is substituted by a straight or branched chain alkyl group having from 1 to 6 carbon atoms; and said substituent β representing a straight or branched chain alkyl group having from 1 to 6 carbon atoms, a straight or branched chain haloalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms, $Y^e$ represents an oxygen atom, a sulfur atom or a group of formula $>N-R^{4e}$ (wherein $R^{4e}$ represents a hydrogen atom, a straight or branched chain alkyl group having from 1 to 3 carbon atoms or a straight or branched chain alkanoyl group having from 2 to 5 carbon atoms), and $Z^e$ represents a 2,4-dioxothiazolidin-5-ylmethyl, 2,4-dioxooxazolidin-5-ylmethyl or 3,5-dioxooxadiazolidin-2-ylmethyl group.

(26) The compounds described in (1), wherein:
$R^{1e}$ represents a hydrogen atom or a straight or branched chain alkyl group having from 1 to 4 carbon atoms,
$R^{2e}$ represents a straight or branched chain alkylene group having from 2 to 5 carbon atoms,
$R^{3e}$ represents a hydrogen atom,
$X^e$ represents an aryl group having from 6 to 10 carbon atoms which is unsubstituted or is substituted by from 1 to 3 substituents selected from the group consisting of substituents α or a heteroaromatic group which has from 5 to 10 ring atoms (and which may have one or two rings) of which from 1 to 3 are hetero-atoms selected from the group consisting of nitrogen, oxygen and sulfur atoms and which is unsubstituted or is substituted by from 1 to 3 substituents selected from the group consisting of substituents α,
said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a fluorine, chorine or bromine atom, (xi) an aralkyl group having from 7 to 12 carbon atoms, (xii) a phenyl group which is unsubstituted or is substituted by at least one substituent selected from the group consisting of substituents β, (xiii) a phenoxy group which is unsubstituted or is substituted by at least one substituent selected from the group consisting of substituents β, (xiv) a phenylthio group which is unsubstituted or is substituted by at least one substituent selected from the group consisting of substituents β, (xv) a phenylsulfonyl group which is unsubstituted or is substituted by at least one substituent selected from the group consisting of substituents β, (xvi) a phenylsulfonylamino group which is unsubstituted or is substituted by at least one substituent selected from the group consisting of substituents β and in which the nitrogen atom of the amino moiety is unsubstituted or is substituted by a straight or branched chain alkyl group having from 1 to 6 carbon atoms, (xvii) a furyl, thienyl, oxazolyl, isoxazolyl, thiazolyl, pyridyl, pyridyloxy, pyridylthio or pyridylsulfonyl group, (xviii) an imidazolyl group in which the nitrogen atom is unsubstituted or is substituted by a straight or branched chain alkyl group having from 1 to 6 carbon atoms and/or (xix) a pyridylsulfonylamino group in which the nitrogen atom of the amino moiety is unsubstituted or is substituted by a straight or branched chain alkyl group having from 1 to 6 carbon atoms; and said substituent β representing a straight or branched chain alkyl group having from 1 to 6 carbon atoms, a straight or branched chain haloalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms, $Y^e$ represents an oxygen atom, and $Z^e$ represents a 2,4-dioxothiazolidin-5-ylmethyl or 2,4-dioxothiazolidin-5-ylmethyl group.

(27) The compounds described in (1), wherein:
$R^{1e}$ represents a hydrogen atom or a straight or branched chain alkyl group having from 1 to 3 carbon atoms,
$R^{2e}$ represents the straight or branched chain alkylene group having 2 or 3 carbon atoms,
$R^{3e}$ represents a hydrogen atom,
$X^e$ represents a phenyl, naphthyl, imidazolyl, oxazolyl, pyridyl, indolyl, quinolyl or isoquinolyl group which is unsubstituted or is substituted by from 1 to 3 substituents selected from the group consisting of substituents α,
said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy group, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a fluorine, chorine or bromine atom, (xi) an aralkyl group having from 7 to 12 carbon atoms, (xii) a phenyl group (which may be substituted with a methyl, trifluoromethyl, methoxy, fluoro or methylenedioxy group), (xiii) a phenoxy group (the phenyl moiety may be substituted with a methyl, trifluoromethyl, methoxy, fluoro or methylenedioxy group), (xiv) a phenylthio group (the phenyl moiety may be substituted with a methyl, trifluoromethyl, methoxy, fluoro or methylenedioxy group), (xv) a phenylsulfonyl group (the phenyl moiety may be substituted with a methyl, trifluoromethyl, methoxy, fluoro or methylenedioxy group), (xvi) a phenylsulfonylamino group (the phenyl moiety may be substituted with a methyl, trifluoromethyl, methoxy, fluoro or methylenedioxy group and the nitrogen atom of the amino moiety may be substituted with a straight or branched chain alkyl group having from 1 to 6 carbon atoms), (xvii) a furyl, thienyl, oxazolyl, isoxazolyl, thiazolyl, pyridyl, pyridyloxy, pyridylthio or pyridylsulfonyl group, (xviii) an imidazolyl group in which the nitrogen atom is unsubstituted or is substituted by a straight or branched chain alkyl group having from 1 to 6 carbon atoms and/or (xix) a pyridylsulfonylamino group in which the nitrogen atom of the amino moiety is unsubstituted or is substituted by a straight or branched chain alkyl group having from 1 to 6 carbon atoms;

$Y^e$ represents an oxygen atom, and $Z^e$ represents a 2,4-dioxothiazolidin-5-ylmethyl group.

(28) The compounds described in (1), wherein:

$R^{1e}$ represents a hydrogen atom, methyl group or ethyl group, $R^{2e}$ represents an ethylene, trimethylene or methylethylene group, $R^{3e}$ represents a hydrogen atom, $X^e$ represents a phenyl, naphthyl, imidazolyl, oxazolyl, pyridyl, indolyl, quinolyl or isoquinolyl group which is unsubstituted or is substituted by from 1 to 3 substituents selected from the group consisting of substituents α, said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain alkanoyloxy group having from 1 to 4 carbon atoms, (v) a straight or branched chain alkoxy group having from 1 to 4 carbon atoms, (vi) a methylenedioxy, benzyloxy, phenethyloxy or naphthylmethoxy group, (vii) a straight or branched chain alkylthio group having from 1 to 4 carbon atoms, (viii) a straight or branched chain alkylsulfonyl group having from 1 to 4 carbon atoms, (ix) a fluorine, chorine or bromine atom, (x) a benzyl group, (xi) a phenyl group (which may be substituted with a methyl, trifluoromethyl, methoxy, fluoro or methylenedioxy group), (xii) a phenoxy group (the phenyl moiety may be substituted with a methyl, trifluoromethyl, methoxy, fluoro or methylenedioxy group), (xiii) a phenylthio, phenylsulfonyl, phenylsulfonylamino, N-methylphenylsulfonylamino, furyl, thienyl, oxazolyl, isoxazolyl, thiazolyl, pyridyl, pyridyloxy, pyridylthio, pyridylsulfonyl, pyridylsulfonylamino, N-methylpyridylsulfonylamino group and/or (xiv) an imidazolyl group in which the nitrogen atom is unsubstituted or is substituted by a straight or branched chain alkyl group having from 1 to 6 carbon atoms;

$Y^e$ represents an oxygen atom, and $Z^e$ represents a 2,4-dioxothiazolidin-5-ylmethyl group.

(29) The compounds described in (1), wherein:

$R^{1e}$ represents a hydrogen atom, a methyl group or an ethyl group, $R^{2e}$ represents an ethylene, trimethylene or methylethylene group, $R^{3e}$ represents a hydrogen atom, $X^e$ represents a phenyl, naphthyl, pyridyl, indolyl, quinolyl or isoquinolyl group which is unsubstituted or is substituted by from 1 to 3 substituents selected from the group consisting of substituents α, said substituents α each representing (i) a straight or branched chain alkyl group having from 1 to 3 carbon atoms, (ii) a trifluoromethyl, difluoromethyl, fluoromethyl, hydroxy, formyloxy or acetoxy group, (iii) a straight or branched chain alkoxy group having from 1 to 3 carbon atoms, (iv) a methylenedioxy, benzyloxy, methylthio, ethylthio, methylsulfonyl or ethylsulfonyl group, (v) a fluorine, chorine or bromine atom, (vi) a benzyl, phenyl, 4-methylphenyl, 4trifluoromethylphenyl, 4-methoxyphenyl, 4-fluorophenyl, 3,4-methyleyedioxyphenyl, phenoxy, phenylthio, phenylsulfonyl, phenylsulfonylamino, N-methylphenylsulfonylamino, furyl, thienyl, oxazolyl, thiazolyl, imidazolyl, N-methylimidazolyl, pyridyl, pyridyloxy, pyridylthio, pyridylsulfonyl, pyridylsulfonylamino and/or N-methylpyridylsulfonylamino group;

$Y^e$ represents an oxygen atom, and $Z^e$ represents a 2,4-dioxothiazolidin-5-ylmethyl group.

(30) The compounds described in (1), wherein:

$R^{1e}$ represents a hydrogen atom, a methyl group or an ethyl group, $R^{2e}$ represents an ethylene group, $R^{3e}$ represents a hydrogen atom, $X^e$ represents a phenyl, naphthyl, pyridyl, quinolyl or isoquinolyl group which is unsubstituted or is substituted by from 1 to 3 substituents selected from the group consisting of substituents α, said substituents α each representing (i) a methyl, ethyl, isopropyl, trifluoromethyl, hydroxy, acetoxy, methoxy, ethoxy, isopropoxy, methylenedioxy, benzyloxy, methylthio, ethylthio, methylsulfonyl, ethylsulfonyl group, chorine atom, benzyl, phenyl, phenoxy, phenylthio, phenylsulfonyl, phenylsulfonylamino, N-methylphenylsulfonylamino, pyridyl, pyridyloxy, pyridylthio, pyridylsulfonyl, pyridylsulfonylamino and/or N-methylpyridylsulfonylamino group;

$Y^e$ represents an oxygen atom, and $Z^e$ represents a 2,4-dioxothiazolidin-5-ylmethyl group.

(31) The compounds described in (1), wherein:

$R^{1e}$ represents a methyl or ethyl group, $R^{2e}$ represents an ethylene group, $R^{3e}$ represents a hydrogen atom, $X^e$ represents a phenyl group which is unsubstituted or is substituted by from 1 to 3 substituents selected from the group consisting of substituents α, said substituents α each representing a methyl, hydroxy, acetoxy, a chlorine atom, benzyl, phenyl, phenoxy, phenylthio, phenylsulfonyl, phenylsulfonylamino, N-methylphenylsulfonylamino, pyridyl, pyridyloxy, pyridylthio and/or pyridylsulfonyl group;

$Y^e$ represents an oxygen atom, and $Z^e$ represents a 2,4-dioxothiazolidin-5-ylmethyl group.

(32) The compounds described in (1), wherein:

$R^{1e}$ represents a methyl or ethyl group, $R^{2e}$ represents an ethylene group, $R^{3e}$ represents a hydrogen atom, $X^e$ represents a pyridyl group which is unsubstituted or is substituted by from 1 to 3 substituents selected from the group consisting of substituents α, said substituents α each representing a methoxy, ethoxy, isopropoxy, benzyloxy, methylthio, ethylthio, methylsulfonyl, ethylsulfonyl, benzyl, phenyl, phenoxy, phenylthio, phenylsulfonyl, phenylsulfonylamino and/or N-methylphenylsulfonylamino;

$Y^e$ represents an oxygen atom, and $Z^e$ represents a 2,4-dioxothiazolidin-5-ylmethyl group.

(33) The compounds described in (1) which are selected from:

i) 5-(4-{2-[(1-biphenyl-4'-ylethylidene)aminooxy]ethoxy}benzyl)thiazolidine-2,4-dione, ii) 5-[4-(2-{[1-(4-phenylsulfonylphenyl)ethylidene]aminooxy}ethoxy)benzyl]thiazolidine-2,4-dione, iii) 5-[4-(2-{[1-(4-pyrid-2'-ylphenyl)ethylidene]aminooxy}ethoxy)benzyl]thiazolidine-2,4-dione (which will hereinafter be called "Compound A"), iv) 5-[4-(2-{[1-(4-pyrid-3'-ylphenyl)ethylidene]aminooxy}ethoxy)benzyl]thiazolidine-2,4-dione, v) 5-[4-(2-{[1-(4-pyrid-4'-ylphenyl)ethylidene]aminooxy}ethoxy)benzyl]thiazolidine-2,4-dione, vi) 5-[4-(2-{[1-(2-phenyl-5-pyridyl)ethylidene]aminooxy}ethoxy)benzyl]thiazolidine-2,4-dione, vii) 5-[4-(2-{[1-(2-methoxy-5-pyridyl)ethylidene]aminooxy}ethoxy)benzyl]thiazolidine-2,4-dione, viii) 5-[4-(2-{[1-(2-ethoxy-5-pyridyl)ethylidene]aminooxy}ethoxy)benzyl]thiazolidine-2,4-dione, ix) 5-[4-(2-{[1-(2-isopropoxy-5-pyridyl)ethylidene]aminooxy}ethoxy)benzyl]thiazolidine-2,4-dione, and x) 5-[4-(2-{[1-(2-benzyl-5-pyridyl)ethylidene]aminooxy}ethoxy)benzyl]thiazolidine-2,4-dione.

(VI) WO95/18125 describes:

(1) an isoxazolidinedione derivative of formula (VI):

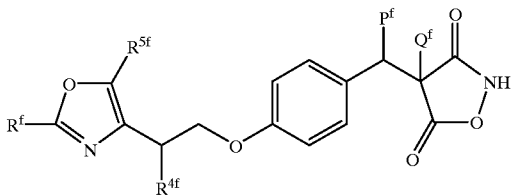

(VI)

wherein:

$R^f$ represents an aromatic hydrocarbon group which may be substituted, a cyclic aliphatic hydrocarbon group which may be substituted, a heterocyclic group which may be substituted, a fused heterocyclic group which may be substituted or a group of formula (VIa):

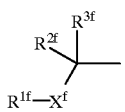

(VIa)

(wherein $R^{1f}$ represents an aromatic hydrocarbon group which may be substituted, a cyclic aliphatic hydrocarbon group which may be substituted, a heterocyclic group which may be substituted or a fused heterocyclic group which may be substituted, $R^{2f}$ and $R^{3f}$ are the same or different and each represents a hydrogen atom or a lower alkyl group, $X^f$ represents an oxygen atom, a sulfur atom or a secondary amino group);

$R^{4f}$ represents a hydrogen atom or a lower alkyl group;

$R^{5f}$ represents a lower alkyl group;

$P^f$ and $Q^f$ each represents a hydrogen atom or together form a bond; and pharmaceutically acceptable salts thereof.

In the compounds of formula (VI), details, such as the definitions of $R^f$, $R^{1f}$, $R^{2f}$, $R^{3f}$, $R^{4f}$, $R^{5f}$, $P^f$ and $Q^f$, the kinds of pharmaceutically acceptable salt, the process for preparing the compounds of formula (VI), examples of the compounds and preparative examples are described in WO95/18125, the disclosure of which is incorporated herein by reference.

More specific examples of the aromatic hydrocarbon groups which may be represented by $R^f$ and $R^{1f}$ include the aryl groups defined and exemplified above in relation to $R^{1d}$.

Where $R^f$ or $R^{1f}$ represents a heterocyclic group or a fused heterocyclic group, this may be any of the aromatic heterocyclic groups or fused heterocyclic groups defined and exemplified above in relation to $A^{1d}$. Alternatively, $R^f$ or $R^{1f}$ may represent a non-aromatic (preferably saturated) heterocyclic group, this may have from 5 to 7 ring atoms, of which from 1 to 3 may be hetero-atoms selected from the group consisting of nitrogen, oxygen and sulfur atoms, at least one preferably being nitrogen. Examples of such groups include the pyrrolidinyl, piperidinyl, piperazinyl, N-methylpiperazinyl, morpholinyl, thiomorpholinyl, oxazolidinyl, thiazolidinyl, diazolidinyl, oxolanyl, thiolanyl and perhydropyridyl groups.

Where $R^f$ or $R^{1f}$ represents a cyclic aliphatic hydrocarbon group, this is preferably a cycloalkyl group, preferably having from 3 to 8 ring carbon atoms, and examples include the cyclopropyl, cyclobutyl, cyclopentyl, cyclohexyl, cycloheptyl and cyclooctyl groups, of which the cyclopentyl and cyclohexyl groups are preferred. Alternatively, it may be a cycloalkenyl group, preferably having from 5 to 8 ring carbon atoms, for example a cyclopentenyl, cyclohexenyl, cycloheptenyl or cyclooctenyl group.

Any of the above groups represented by $R^f$ or $R^{1f}$ may be substituted or unsubstituted. If substituted, the group may be substituted by any group commonly used in the field, for example, those defined and exemplified above in relation to substituents α.

Where $R^{2f}$, $R^{3f}$, $R^{4f}$, or $R^{5f}$ represents an alkyl group, this is a lower alkyl group preferably having from 1 to 6 carbon atoms, more preferably having from 1 to 4 carbon atoms, and may be as defined and exemplified above in relation to $R^{3c}$ and substituents χ.

Preferred examples of compounds of formula (VI) include:

(2) The compound described in (1), wherein $R^{4f}$ represents a hydrogen atom and $R^{5f}$ represents a lower alkyl group.

(3) The compound described in (2), wherein $R^f$ represents a phenyl group which may be substituted, a 5- or 6-membered aromatic heterocyclic group which may be substituted and has 1 or 2 hetero atoms selected from the group consisting of sulfur, oxygen and nitrogen atoms, or a fused aromatic heterocyclic group which may be substituted and is formed by fusing the above-described aromatic heterocyclic ring with a benzene ring.

(4) The compound described in (3), wherein $R^f$ represents a phenyl group, a 5- or 6-membered aromatic heterocyclic group having 1 to 2 hetero atoms selected from the group consisting of sulfur, oxygen and nitrogen atoms, or a fused aromatic heterocyclic group formed by fusing the above-described aromatic heterocyclic ring with a benzene ring.

(5) The compound described in (3), wherein $R^f$ represents a phenyl group or a fused aromatic heterocyclic group formed by fusing a benzene ring with a 5- or 6-membered heterocyclic ring having a sulfur atom.

(6) The compound described in (2), wherein $R^f$ represents a phenyl, benzothienyl or 1-methyl-1-(2-pyridylthio) methyl group.

(7) The compound described in (2), wherein $R^f$ represents a phenyl group.

(8) The compound described in (2), wherein $R^f$ represents a group of formula (VIa):

(9) The compound described in (8), wherein $R^{1f}$ represents a phenyl group which may be substituted or a 5- or 6-membered aromatic heterocyclic group which has 1 to 2 hetero atoms selected from the group consisting of sulfur, oxygen and nitrogen atoms and which may be substituted.

(10) The compound described in (8), wherein $R^{1f}$ represents a 5- or 6-membered aromatic heterocyclic group which has 1 to 2 hetero atoms selected from the group consisting of sulfur, oxygen and nitrogen atoms.

(11) The compound described in (8), wherein $R^{1f}$ represents a 5- or 6-membered aromatic heterocyclic group having a nitrogen atom.

(12) The compound described in (8), wherein $R^{1f}$ represents a pyridyl group.

(13) The compounds described in (1) which are selected from:

i) 4-{4-[2-(2-phenyl-5-methyl-4-oxazolyl)ethoxy]benzyl}-3,5-isoxazolidinedione, ii) 4-{4-[2-(2-phenyl-5-methyl-4-oxazolyl)ethoxy]benzylidene}-3,5-isoxazolidinedione, iii) 4-{4-[2-(2-benzothienyl-5-methyl-4-oxazolyl)ethoxy]benzyl}-3,5-isoxazolidinedione and iv) 4-[4-(2-{5-methyl-2-[1-(2-pyridylthio)ethyl]-4-oxazolyl}ethoxy)benzyl]-3,5-isoxazolidinedione.

(VII) Japanese Patent Application Kokai No. Hei 7-330728 or European Patent Publication No. 676398A describes:

(1) a heterocyclic compound of formula (VII):

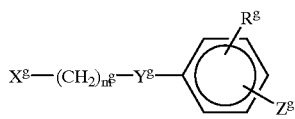

wherein:

$X^g$ represents an indole, indoline, azaindole, azaindoline, imidazopyridine or imidazopyrimidine ring group which is unsubstituted or is substituted by from 1 to 3 substituents selected from the group consisting of substituents δ, defined below;

$Y^g$ represents an oxygen or sulfur atom;

$Z^g$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethyl group;

$R^g$ represents a hydrogen atom, a straight or branched chain alkyl group having from 1 to 4 carbon atoms, a straight or branched chain alkoxy group having from 1 to 4 carbon atoms, a halogen atom, a hydroxy group, a nitro group, an amino group which is unsubstituted or is substituted by at least one substituent selected from the group consisting of substituents ε, defined below, or a straight or branched chain aralkyl group having from 7 to 11 carbon atoms;

said substituent ε represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 11 carbon atoms; and $m^g$ represents an integer of from 1 to 5, said substituent δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined above, an aryl group having from 6 to 10 carbon atoms which is unsubstituted or is substituted by at least one substituent selected from the group consisting of substituents φ, or a straight or branched chain aralkyl group having from 7 to 11 carbon atoms which is unsubstituted or is substituted by at least one substituent selected from the group consisting of substituents φ;

said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents ε, defined above;

and pharmaceutically acceptable salts thereof.

In the compounds of formula (VII), details, such as the definitions of $R^g$, $X^g$, $Y^g$, $m^g$ and $Z^g$ and substituents δ, ε and φ, the kinds of pharmaceutically acceptable salt, the process for preparing the compounds of formula (VII), examples of the compounds and preparative examples are described in Japanese Patent Application Kokai No. Hei 7-330728 or European Patent Publication No. 676398A, the disclosures of which are incorporated herein by reference.

For example, where $R^g$, substituent δ or substituent φ represents an alkyl or alkoxy having from 1 to 4 carbon atoms, this may be as defined and exemplified above in relation to substituent χ. Where $R^g$ or substituent ε represents an aralkyl group, this may be as defined and exemplified above in relation to $R^{1d}$. Where substituent δ represents an alkylthio group, this may be as defined and exemplified above in relation to $W^{2c}$. Where substituent δ or substituent ε represents an aryl group, this may be as defined and exemplified above in relation to $R^{1d}$. Where substituent ε represents a straight or branched chain aliphatic acyl group having from 1 to 11 carbon atoms, an aromatic aliphatic acyl group having from 8 to 12 carbon atoms or an aromatic acyl group having from 7 to 11 carbon atoms, these may be selected from the coresponding groups defined and exemplified above in relation to $R^{1d}$.

Preferred examples of the compounds of formula (VII) include:

(2) The compounds described in (1), wherein $X^g$ represents an indole, indoline, azaindole, imidazopyridine or imidazopyrimidine ring group which is unsubstituted or is substituted by from 1 to 3 substituents selected from the group consisting of substituents δ, defined below;

said substituents δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined below, an aryl group having from 6 to 10 carbon atoms which is unsubstituted or is substituted by at least one substituent selected from the group consisting of substituents φ, defined below, or a straight or branched chain aralkyl group having from 7 to 11 carbon atoms which is unsubstituted or is substituted by at least one substituent selected from the group consisting of substituents φ, defined below;

said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents ε, defined below;

said substituent ε represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 11 carbon atoms;

(3) The compounds described in (1), wherein $X^g$ represents an indole, indoline, imidapyridine or imidazopyrimidine ring group which is unsubstituted or is substituted by from 1 to 3 substituents selected from the group consisting of substituents δ, defined below;

said substituents δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined below, an aryl group having from 6 to 10 carbon atoms which is unsubstituted or is substituted by at least one substituent selected from the group consisting of substituents φ, defined below, or a straight or branched chain aralkyl group having from 7 to 11 carbon atoms which is unsubstituted or is substituted by at least one substituent selected from the group consisting of substituents φ, defined below.

said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents ε, defined below;

said substituent ε represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 11 carbon atoms.

(4) The compounds described in (1), wherein $X^g$ represents an indole, indoline or imidazopyridine ring group which is unsubstituted or is substituted by from 1 to 3 substituents selected from the group consisting of substituents δ, defined below;

said substituents δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined below, an aryl group having from 6 to 10 carbon atoms which is unsubstituted or is substituted by from 1 to 3 substituents selected from the group consisting of substituents φ, defined below, or a straight or branched chain aralkyl group having from 7 to 11 carbon atoms which is unsubstituted or is substituted by from 1 to 3 substituents selected from the group consisting of substituents φ, defined below;

said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents ε, defined below;

said substituent ε represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 11 carbon atoms.

(5) The compounds described in (1), wherein $X^g$ represents an indoline or imidazopyridine ring group which is unsubstituted or is substituted by from 1 to 3 substituents selected from the group consisting of substituents δ, defined below;

said substituent δ represents a straight or branched chain alkyl group having from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group or a phenyl group.

(6) The compounds described in (1), wherein $X^g$ represents an imidazopyridine ring group which is unsubstituted or is substituted by from 1 to 3 substituents selected from the group consisting of substituents δ, defined below;

said substituent δ represents a methyl, ethyl, isopropyl, methoxy, ethoxy, propoxy, isopropoxy, benzyloxy, fluorine, chlorine, phenylthio, methylthio, ethylthio or a phenyl group.

(7) The compounds described in (1), wherein $R^g$ represents a hydrogen atom, a straight or branched chain alkyl group having from 1 to 4 carbon atoms, a straight or branched chain alkoxy group having from 1 to 4 carbon atoms or a halogen atom.

(8) The compounds described in (1), wherein $R^g$ represents a hydrogen atom, a methoxy group, an ethoxy group, a fluorine atom or a chlorine atom.

(9) The compounds described in (1), wherein $R^g$ represents a hydrogen atom or a methoxy group.

(10) The compound described in (1), wherein $R^g$ represents a hydrogen atom.

(11) The compound described in (1), wherein $Y^g$ represents an oxygen atom.

(12) The compound described in (1), wherein $Z^g$ represents a 2,4-dioxothiazolidin-5-ylidenylmethyl, 2,4-dioxothiazolidin-5-ylmethyl or 2,4-dioxooxazolidin-5-ylmethyl group.

(13) The compound described in (1), wherein $Z^g$ represents a 2,4-dioxothiazolidin-5-ylidenylmethyl or 2,4-dioxothiazolidin-5-ylmethyl group;

(14) The compound described in (1), wherein $Z^g$ represents a 2,4-dioxothiazolidin-5-ylmethyl group.

(15) The compounds described in (1), wherein:

$X^g$ represents an indole, indoline, azaindole, imidazopyridine or imidazopyrimidine ring group which is unsubstituted or is substituted by from 1 to 3 substituents selected from the group consisting of substituents δ, defined below;

$Y^g$ represents an oxygen or sulfur atom;

$Z^g$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-yhnethyl or N-hydroxyureidomethyl group;

$R^g$ represents a hydrogen atom, a straight or branched chain alkyl group having from 1 to 4 carbon atoms, a straight or branched chain alkoxy group having from 1 to 4 carbon atoms or a halogen atom, and $m^g$ represents an integer of from 1 to 5;

said substituent δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined below, an aryl group having from 6 to 10 carbon atoms which is unsubstituted or is substituted by at least one substituent selected from the group consisting of substituents φ, defined below, or a straight or branched chain aralkyl group having from 7 to 11 carbon atoms which is unsubstituted or is substituted by at least one substituent selected from the group consisting of substituents φ, defined below;

said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group, an amino group which is unsubstituted or is substituted by at least one substituent selected from the group consisting of substituents ε, defined below;

said substituent ε represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 11 carbon atoms.

(16) The compounds described in (1), wherein:

$X^g$ represents an indole, indoline, imidazopyridine or imidazopyrimidine ring group which is unsubstituted or is substituted by from 1 to 3 substituents selected from the group consisting of substituents δ, defined below;

$Y^g$ represents an oxygen atom;

$Z^g$ represents a 2,4-dioxothiazolidin-5-ylidenylmethyl, 2,4-dioxothiazolidin-5-ylmethyl or 2,4-dioxooxazolidin-5-ylmethyl group;

$R^g$ represents a hydrogen atom, a straight or branched chain alkyl group having from 1 to 4 carbon atoms, a straight or branched chain alkoxy group having from 1 to 4 carbon atoms or halogen atom; and $m^g$ represents an integer of from 1 to 5;

said substituent δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined below, an aryl group having from 6 to 10 carbon atoms which is unsubstituted or is substituted by at least one substituent selected from the group consisting of substituents φ, defined below, or a straight or branched chain aralkyl group having from 7 to 11 carbon atoms which is unsubstituted or is substituted by at least one substituent selected from the group consisting of substituents φ, defined below;

said substituent ε represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 12 carbon atoms;

said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents ε, defined above.

(17) The compounds described in (1), wherein:

$X^g$ represents an indole, indoline or imidazopyridine ring group which is unsubstituted or is substituted by from 1 to 3 substituents selected from the group consisting of substituents δ, defined below;

$Y^g$ represents an oxygen atom;

$Z^g$ represents a 2,4-dioxothiazolidin-5-ylidenylmethyl or 2,4-dioxothiazolidin-5-ylmethyl group;

$R^g$ represents a hydrogen atom, a methoxy group, an ethoxy group, a fluorine atom or a chlorine atom; and m$^g$ represents an integer of from 1 to 5;

said substituent δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined below, an aryl group having from 6 to 10 carbon atoms which is unsubstituted or is substituted by from 1 to 3 substituents selected from the group consisting of substituents φ, defined below, or a straight or branched chain aralkyl group having from 7 to 11 carbon atoms which is unsubstituted or is substituted by from 1 to 3 substituents selected from the group consisting of substituents φ, defined below;

said substituent ε represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 11 carbon atoms;

said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents ε, defined above.

(18) The compounds described in (1), wherein:

X$^g$ represents an indoline or imidazopyridine ring group which is unsubstituted or is substituted by from 1 to 3 substituents selected from the group consisting of substituents δ, defined below;

Y$^g$ represents an oxygen atom;

Z$^g$ represents a 2,4-dioxothiazolidin-5-ylmethyl group;

R$^g$ represents a hydrogen atom or a methoxy group; and m$^g$ represents an integer of from 1 to 5;

said substituent δ represents a straight or branched chain alkyl group having from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group or a phenyl group.

(19) The compounds described in (1), wherein:

X$^g$ represents an imidazopyridine ring group which is unsubstituted or is substituted by from 1 to 3 substituents selected from the group consisting of substituents δ, defined below;

Y$^g$ represents an oxygen atom;

Z$^g$ represents a 2,4-dioxothiazolidin-5-ylmethyl group;

R$^g$ represents a hydrogen atom; and m$^g$ represents an integer of from 1 to 5;

said substituent δ represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group or a phenyl group.

(20) The compounds described in (1) which are selected from:

i) 5-{4-(3-methylimidazo[4,5-b]pyridin-2-ylmethoxy)benzyl}thiazolidine-2,4-dione, ii) 5-{4-(5-chloro-3-methylimidazo[4,5-b]pyridin-2-ylmethoxy)benzyl}thiazolidine-2,4-dione, iii) 5-{4-(5-methoxy-3-methylimidazo[4,5-b]pyridin-2-ylmethoxy)benzyl}thiazolidine-2,4-dione, iv) 5-{4-(5-hydroxy-3-methylimidazo[4,5-b]pyridin-2-ylmethoxy)benzyl}thiazolidine-2,4-dione, v) 5-{4-(5-ethoxy-3-methylimidazo[4,5-b]pyridin-2-ylmethoxy)benzyl}thiazolidine-2,4-dione, vi) 5-{4-(5-isopropoxy-3-methylimidazo[4,5-b]pyridin-2-ylmethoxy)benzyl}thiazolidine-2,4-dione, and vii) 5-[4-(1-methylindolin-2-ylmethoxy)benzyl]thiazolidine-2,4-dione.

(VIII) European Patent Publication No. 745600A describes:

(1) a fused heterocyclic compound of formula (VIII):

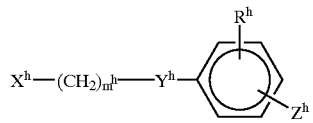

(VIII)

wherein:

X$^h$ represents a benzimidazole ring group which is unsubstituted or is substituted by from 1 to 5 substituents selected from the group consisting of substituents γ, defined below, Y$^h$ represents an oxygen or sulfur atom, Z$^h$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethyl group;

R$^h$ represents a hydrogen atom, a straight or branched chain alkyl group having from 1 to 4 carbon atoms, a straight or branched chain alkoxy group having from 1 to 4 carbon atoms, a halogen atom, a hydroxy group, a nitro group, an amino group which is unsubstituted or is substituted by at least one substituent selected from the group consisting of substituents η, defined below, or a straight or branched chain aralkyl group having from 7 to 11 carbon atoms, and m$^h$ represents an integer of from 1 to 5, said substituent γ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents η, defined below, an aryl group having from 6 to 10 carbon atoms which is unsubstituted or is substituted by at least one substituent selected from the group consisting of substituents λ, defined below, or a straight or branched chain aralkyl group having from 7 to 11 carbon atoms which is unsubstituted or is substituted by at least one substituent selected from the group consisting of substituents λ, defined below;

said substituent η represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, a aromatic aliphatic acyl group having from 8 to 12 carbon atoms or an aromatic acyl group having from 7 to 11 carbon atoms.

said substituent λ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents η, defined above;

and pharmaceutically acceptable salts thereof.

In the compounds of formula (VIII), details, such as the definitions of $R^h$, $X^h$, $Y^h$ $Z^h$ and substituents γ, η and λ and $m^h$, the kinds of pharmaceutically acceptable salt, the preparation process for the compounds of formula (VIII), examples of the compounds and preparative examples are described in European Patent Publication No. 745600A, the disclosure of which is incorporated herein by reference.

Where $R^h$, substituent γ or substituent λ represents an alkyl or alkoxy group, this has from 1 to 4 carbon atoms, and may be any of the coresponding groups defined and exemplified above in relation to substituent χ. Where $R^h$, substituent γ or substituent η represents an aralkyl group, this may be as defined and exemplified above in relation to $R^{1d}$. Where substituent γ or substituent η represents a halogen atom, this may be as defined and exemplified above in relation to substituent χ. Where substituent γ represents an alkylthio group, this may be as defined and exemplified above in relation to $W^{2c}$. Where substituent γ represents an aryl group, this may be as defined and exemplified above in relation to $R^{1d}$. Where substituent η represents a straight or branched chain aliphatic acyl group having from 1 to 11 carbon atoms, an aromatic aliphatic acyl group having from 8 to 12 carbon atoms or an aromatic acyl group having from 7 to 11 carbon atoms, these may be selected from the coresponding groups defined and exemplified above in relation to $R^{1d}$.

Where substituent η represents an alkyl group having from 1 to 8 carbon atoms, this may be a straight or branched chain group, and examples include the methyl, ethyl, propyl, isopropyl, butyl, isobutyl, sec-butyl, t-butyl, pentyl, isopentyl, neopentyl, 2-methylbutyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, heptyl and octyl groups. Of these, we prefer those alkyl groups having from 1 to 4 carbon atoms, particularly the methyl, ethyl, propyl, isopropyl, butyl and isobutyl groups, and most preferably the methyl group.

Preferred examples of the compounds of formula (VIII) include:

(2) The compound described in (1), wherein $R^h$ represents a hydrogen atom, a straight or branched chain alkyl group having from 1 to 4 carbon atoms, a straight or branched chain alkoxy group having from 1 to 4 carbon atoms or a halogen atom.

(3) The compound described in (1), wherein $Y^h$ represents an oxygen atom.

(4) The compound described in (1), wherein $Z^h$ represents a 2,4-dioxothiazolidin-5-ylmethyl, 2,4-dioxothiazolidin-5-ylidenylmethyl or 2,4-dioxooxazolidin-5-ylmethyl group.

(5) The compound described in (1), wherein:
$R^h$ represents a hydrogen atom, a straight or branched chain alkyl group having from 1 to 4 carbon atoms, a straight or branched chain alkoxy group having from 1 to 4 carbon atoms or a halogen atom,
$Y^h$ represents an oxygen atom, and
$Z^h$ represents a 2,4-dioxothiazolidin-5-ylmethyl, 2,4-dioxothiazolidin-5-ylidenylmethyl or 2,4-dioxooxazolidin-5-ylmethyl group.

(6) The compound described in (1), wherein $Z^h$ represents a 2,4-dioxothiazolidin-5-ylmethyl or 2,4-dioxothiazolidin-5-ylidenylmethyl group.

(7) The compound described in (1), wherein $R^h$ represents a hydrogen atom, a methyl group, a methoxy group, an ethoxy group, a fluorine atom or a chlorine atom.

(8) The compound described in (1), wherein $m^h$ represents an integer of from 1 to 3.

(9) The compound described in (1), wherein:
$Y^h$ represents an oxygen atom,
$Z^h$ represents a 2,4-dioxothiazolidin-5-ylmethyl or 2,4-dioxothiazolidin-5-ylidenylmethyl group,
$R^h$ represents a hydrogen atom, a methyl group, a methoxy group, an ethoxy group, a fluorine atom or a chlorine atom, and
$m^h$ represents an integer of from 1 to 3.

(10) The compound described in (1), wherein $X^h$ represents a benzimidazole ring group which is unsubstituted or is substituted by from 1 to 5 substituents selected from the group consisting of substituents γ, defined below;
said substituent γ represents a straight or branched chain alkyl group having from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group, a hydroxy group, an acetoxy group, a benzyl group or a phenyl group.

(11) The compound described in (1), wherein $Z^h$ represents a 2,4-dioxooxazolidin-5-ylmethyl group.

(12) The compound described in (1), wherein $R^h$ represents a hydrogen atom, a methyl group or a methoxy group.

(13) The compound described in (1), wherein:
$X^h$ represents a benzimidazole ring group which is unsubstituted or is substituted by from 1 to 5 substituents selected from the group consisting of substituents γ, defined below;
said substituent γ represents a straight or branched chain alkyl group having from 1 to 4 carbon atoms, a straight or branched chain alkoxy group having from 1 to 4 carbon atoms, a benzyloxy group, a halogen atom, a phenylthio group, a straight or branched chain alkylthio group having from 1 to 4 carbon atoms, a trifluoromethyl group, a hydroxy group, an acetoxy group, a benzyl group or a phenyl group,
$Y^h$ represents an oxygen atom,
$Z^h$ represents a 2,4-dioxooxazolidin-5-ylmethyl group,
$R^h$ represents a hydrogen atom, a methyl group or a methoxy group, and
$m^h$ represents an integer of from 1 to 3.

(14) The compound described in (1), wherein $X^h$ represents a benzimidazole ring group which is unsubstituted or is substituted by from 1 to 5 substituents selected from the group consisting of substituents γ, defined below;
said substituent γ represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group or a phenyl group.

(15) The compound described in (1), wherein $R^h$ represents a hydrogen atom.

(16) The compound described in (1), wherein $m^h$ represents 1 or 2.

(17) The compound described in (1), wherein:

$X^h$ represents a benzimidazole ring group which is unsubstituted or is substituted by from 1 to 5 substituents selected from the group consisting of substituents γ, defined below;

said substituent γ represents a methyl group, an ethyl group, an isopropyl group, a methoxy group, an ethoxy group, a propoxy group, an isopropoxy group, a benzyloxy group, a fluorine atom, a chlorine atom, a phenylthio group, a methylthio group, an ethylthio group, a hydroxy group, an acetoxy group, a benzyl group or a phenyl group;

$Y^h$ represents an oxygen atom;

$Z^h$ represents a 2,4-dioxothiazolidin-5-ylmethyl group;

$R^h$ represents a hydrogen atom; and $m^h$ represents 1 or 2.

(18) The compound described in (1), wherein $X^h$ represents a benzimidazole ring group which is unsubstituted or is substituted by from 1 to 5 substituents selected from the group consisting of substituents γ, defined below;

said substituent γ represents a methyl, methoxy, hydroxy, acetoxy or benzyl group.

(19) The compound described in (1), wherein $m^h$ represents 1.

(20) The compound described in (1), wherein:

$X^h$ represents a benzimidazole ring group which is unsubstituted or is substituted by from 1 to 5 substituents selected from the group consisting of substituents γ, defined below;

said substituent γ represents a methyl group, a methoxy group, a hydroxy group, an acetoxy group or a benzyl group, $Y^h$ represents an oxygen atom, $Z^h$ represents a 2,4-dioxothiazolidin-5-ylmethyl group, $R^h$ represents a hydrogen atom, and $m^h$ represents 1.

(21) The compounds described in (1) which are selected from:

i) 5-[4-(1-methylbenzimidazol-2-ylmethoxy)benzyl]thiazolidine-2,4-dione, ii) 5-[4-(6-methoxy-1-methylbenzimidazol-2-ylmethoxy)benzyl]thiazolidine-2,4-dione (which will hereinafter be called "Compound B"), iii) 5-[4-(5-methoxy-1-methylbenzimidazol-2-ylmethoxy)benzyl]thiazolidine-2,4-dione, iv) 5-[4-(1-benzylbenzimidazol-5-ylmethoxy)benzyl]thiazolidine-2,4-dione, v) 5-[4-(5-hydroxy-1,4,6,7-tetramethylbenzimidazol-2-ylmethoxy)benzyl]thiazolidine-2,4-dione, and vi) 5-[4-(5-acetoxy-1,4,6,7-tetramethylbenzimidazol-2-ylmethoxy)benzyl]-thiazolidine-2,4-dione.

(IX) Japanese Patent Application Kokai No. Hei 1-272574 and European Patent Publication No. 332332A describe:

(1) A compound of formula (IX):

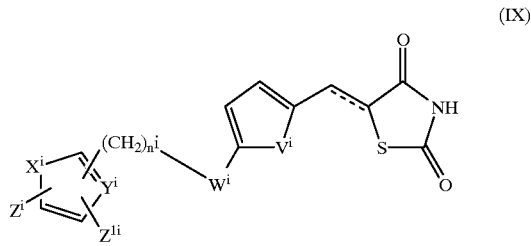

wherein:

=== represents a single or double bond;

$V^i$ represents a group of formula —CH=CH—, —N=CH— or —CH=N— or a sulfur atom;

$W^i$ represents a group of formula >$CH_2$, >CHOH, >CO, >C=NOR$^i$ or —CH=CH—, $X^i$ represents a sulfur or oxygen atom or a group of formula >NR$^{1i}$; —CH=N— or —N=CH—, $Y^i$ represents a group of formula =CH— or a nitrogen atom, $Z^i$ represents a hydrogen atom, an alkyl group having from 1 to 7 carbon atoms, a cycloalkyl group having from 3 to 7 carbon atoms, a phenyl group, a naphthyl group, a pyridyl group, a furyl group, a thienyl group or a phenyl group substituted with one or two substituents selected from the group consisting of alkyl groups having from 1 to 3 carbon atoms, trifluoromethyl groups, alkoxy groups having from 1 to 3 carbon atoms, fluorine atoms, chlorine atoms and bromine atoms, $Z^{1i}$ represents a hydrogen atom or an alkyl group having from 1 to 3 carbon atoms, $R^i$ and $R^{1i}$ each independently represents a hydrogen atom or a methyl group, and $n^i$ represents 1, 2 or 3;

and pharmaceutically acceptable salts thereof.

In the compounds of formula (IX), details, such as the definitions of $V^i$, $W^i$, $X^i$, $Y^i$, $Z^i$, $Z^{1i}$, $R^i$, $R^{1i}$ and $n^i$, the kinds of pharmaceutically acceptable salt, the process for preparing the compounds of formula (IX), examples of the compounds and preparative examples are described in Japanese Patent Application Kokai No. Hei 1-272574 and European Patent Publication No. 332332A, the disclosures of which are incorporated herein by reference.

For example, where $Z^i$ represents an alkyl group having from 1 to 7 carbon atoms or $Z^{1i}$ or the substituent on the phenyl group represented by $Z^i$ represents an alkyl group having from 1 to 3 carbon atoms, these may be selected among the coresponding groups defined and exemplified above in relation to substituents η. Where $Z^i$ represents a cycloalkyl group having from 3 to 7 carbon atoms, this may be a cyclopropyl, cyclobutyl, cyclopentyl, cyclohexyl or cycloheptyl group.

Preferred examples of the compounds of formula (IX) include:

(2) The compounds described in (1), wherein the broken line is no bond and $W^i$ represents a group of formula >CO or >CHOH.

(3) The compounds described in (2), wherein $V^i$ represents a group of formula —CH=CH— or —CH=N— or a sulfur atom, and $n^i$ represents 2.

(4) The compounds described in (3), wherein $X^i$ represents an oxygen atom, $Y^i$ represents N which forms an oxazol-4-yl group, $Z^i$ represents the (2-thienyl), (2-furyl), phenyl, substituted phenyl or naphthyl group and $Z^{1i}$ represents the 5-methyl group.

(5) The compounds described in (4), wherein $V^i$ represents a group of formula —CH=N— or a sulfur atom, and $Z^i$ represents a 2-phenyl group.

(6) The compounds described in (1), wherein $V^i$ represents a group of formula —CH=CH—, $W^i$ represents a group of formula >CO, and $Z^i$ represents a 2-(2-furyl), 2-phenyl, 2-(4-methylphenyl) or 2-(2-naphthyl) group.

(7) The compounds described in (3), wherein $X^i$ represents an oxygen or sulfur atom, and $Y^i$ represents a nitrogen atom, which forms an oxazol-5-yl group, a thiazol-4-yl group or a thiazol-5-yl group.

(8) The compounds described in (3), wherein $X^i$ represents a group of formula —CH=N— and $Y^i$ represents CH which forms a pyrid-2-yl; or $X^i$ represents an oxygen atom and $Y^i$ represents CH which forms a fur-2-yl group.

(9) The compound described in (1), which is 5-{4-[3-(5-methyl-2-phenyloxazol-4-yl)propionyl]benzyl}thiazolidine-2,4-dione.

(X) Japanese Patent Application Kokai No. 6-247945 and European Patent Publication No. 604983A describe:

(1) a naphthalene derivative of formula (X):

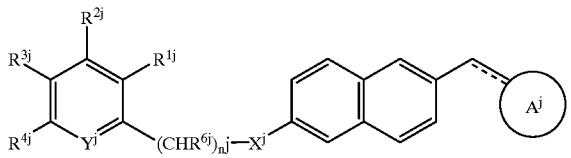

wherein:

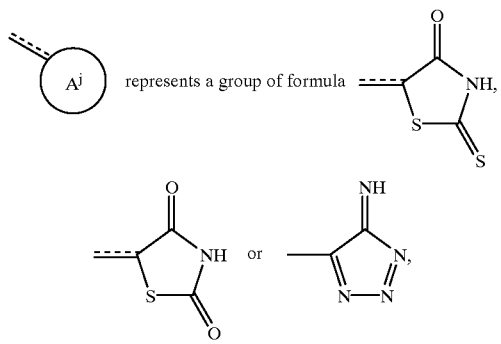

represents a group of formula

—$X^j$— represents an oxygen or sulfur atom;
=$Y^j$— represents =N— or a group of formula =$CR^{5j}$—;
$R^{1j}$, $R^{2j}$, $R^{3j}$, $R^{4j}$ and $R^{5j}$ each independently represents a hydrogen atom, a halogen atom, an alkyl group, an aryl group, an alkoxy group, an alkoxyalkoxy group, an aryloxy group, an alkanoyloxy group, an arylcarbonyloxy group, a carboxyl group, an alkoxycarbonyl group, an aryloxycarbonyl group, a carbamoyl group, an alkylaminocarbonyl group, an arylaminocarbonyl group, an amino group, an alkylamino group, an alkanoylamino group, an arylcarbonylamino group, an ethylenedioxymethyl group, a formyl group, a cyano group, a nitro group or a trihalomethyl group, $R^{6j}$ represents a hydrogen atom, an alkyl group which may be substituted or an aryl group which may be substituted, and $n^j$ represents 0 or an integer of from 1 to 3;
and ==== represent a single or double bond;
and pharmaceutically acceptable salts thereof.

In the compounds of formula (X), details, such as the definitions of $A^j$, $X^j$, $Y^j$, $R^{1j}$, $R^{2j}$, $R^{3j}$, $R^{4j}$, $R^{5j}$, $R^{6j}$ and $n^j$, the kinds of pharmaceutically acceptable salt, the process for preparing the compounds of formula (X), examples of the compounds and preparative examples are described in Japanese Patent Application Kokai No. 6-247945 and European Patent Publication No. 604983A, the disclosures of which are incorporated herein by reference.

Where $R^{1j}$, $R^{2j}$, $R^{3j}$, $R^{4j}$ or $R^{5j}$ represents a halogen atom, an alkyl group, an aryl group or an alkoxy group, these may be as defined and exemplified above in relation to substituent $\chi$, $R^{3c}$ or $R^{4a}$, respectively. Where $R^{1j}$, $R^{2j}$, $R^{3j}$, $R^{4j}$ or $R^{5j}$ represents an alkoxyalkoxy group, an aryloxy group, an alkanoyloxy group, an arylcarbonyloxy group, an alkoxycarbonyl group, an aryloxycarbonyl group, an alkylaminocarbonyl group, an arylaminocarbonyl group, an alkanoylamino group or an arylcarbonylamino group, the respective parts of these groups may be as defined and exemplified above.

Where $R^{1j}$, $R^{2j}$, $R^{3j}$, $R^{4j}$ or $R^{5j}$ represents an alkylamino group, this may be a mono- or di- alkylamino group as defined and exemplified above in relation to substituent $\chi$.

Where $R^{1j}$, $R^{2j}$, $R^{3j}$, $R^{4j}$ or $R^{5j}$ represents a trihalomethyl group, this may be a trifluoromethyl, trichloromethyl, tribromomethyl or triiodomethyl group, preferably a trifluoromethyl group.

Preferred examples of compounds of formula (X) include:

(2) The compounds described in (1), wherein $R^{1j}$, $R^{2j}$, $R^{3j}$, $R^{4j}$ i and $R^{5j}$ each independently represents a hydrogen atom, a halogen atom, an alkyl group having from 1 to 8 carbon atoms, an aryl group having from 6 to 12 carbon atoms, an alkoxy group having from 1 to 8 carbon atoms, an alkoxyalkoxy group having from 2 to 6 carbon atoms, an aryloxy group having from 6 to 12 carbon atoms, an alkanoyloxy group having from 2 to 9 carbon atoms, an arylcarbonyloxy group having from 7 to 13 carbon atoms, a carboxyl group, an alkoxycarbonyl group having from 2 to 9 carbon atoms, an aryloxycarbonyl group having from 7 to 13 carbon atoms, a carbamoyl group, an alkylaminocarbonyl group having from 2 to 9 carbon atoms, an arylaminocarbonyl group having from 7 to 13 carbon atoms, an amino group, an alkylamino group having from 1 to 8 carbon atoms, an alkanoylamino group having from 2 to 9 carbon atoms, an arylcarbonylamino group having from 7 to 13 carbon atoms, an ethylenedioxymethyl group, a formyl group, a cyano group, a nitro group or a trihalomethyl group, and $R^{6j}$ represents a hydrogen atom, an alkyl group having from 1 to 8 carbon atoms which is unsubstituted or is substituted by at least one substituent selected from the group consisting of phenyl groups, halogen atoms, nitro groups and cyano groups or an aryl group having from 6 to 12 carbon atoms which is unsubstituted or is substituted by at least one substituent selected from the group consisting of alkyl groups having from 1 to 8 carbon atoms, halogen atoms, nitro groups and cyano groups.

(3) The compounds described in (1), wherein:
$R^{1j}$, $R^{2j}$, $R^{3j}$, $R^{4j}$ and $R^{5j}$ each independently represents a hydrogen atom, a halogen atom, an alkyl group having from 1 to 8 carbon atoms, an alkoxy group having from 1 to 8 carbon atoms, an alkoxyalkoxy group having from 2 to 6 carbon atoms, an alkanoyloxy group having from 2 to 9 carbon atoms, an arylcarbonyloxy group having from 7 to 13 carbon atoms, a carboxyl group, an alkoxycarbonyl group having from 2 to 9 carbon atoms, a carbamoyl group, alkylaminocarbonyl group having from 2 to 9 carbon atoms, an arylaminocarbonyl group having from 7 to 13 carbon atoms, an amino group, an alkylamino group having from 1 to 8 carbon atoms, an alkanoylamino group having from 2 to 9 carbon atoms, an arylcarbonylamino group having from 7 to 13 carbon atoms, an ethylenedioxymethyl group, a formyl group, a cyano group, a nitro group or trihalomethyl group; and $R^{6j}$ represents a hydrogen atom, an alkyl group having from 1 to 8 carbon atoms or an aryl group having from 6 to 12 carbon atoms which may be substituted with a halogen atom.

(4) The compounds described in (1), wherein:

—$X^j$— represents an oxygen atom;

$Y^i$ represents a group of formula =$CR^{5j}$—;

$R^{1j}$, $R^{2j}$, $R^{3j}$, $R^{4j}$ and $R^{5j}$ each independently represents a hydrogen atom, a halogen atom, an alkyl group having from 1 to 5 carbon atoms, an alkoxy group having from 1 to 5 carbon atoms, an alkoxyalkoxy group having from 2 to 6 carbon atoms, an alkanoyloxy group having from 2 to 6 carbon atoms, a carboxyl group, an alkoxycarbonyl group having from 2 to 6 carbon atoms, an arylaminocarbonyl group having from 7 to 13 carbon atoms, an amino group, an alkanoylamino group having from 2 to 6 carbon atoms, an ethylenedioxymethyl group, a formyl group, a cyano group, a nitro group or a trihalomethyl group; and $R^{6j}$ represents a hydrogen atom, an alkyl group having from 1 to 5 carbon atoms or an aryl group having from 6 to 12 carbon atoms which may be substituted with a halogen atom.

(5) The compounds described in (1),

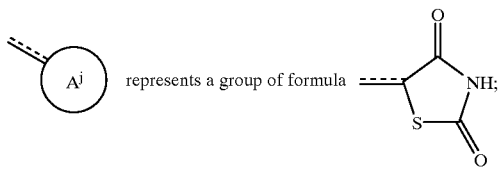 represents a group of formula

—$X^j$— represents an oxygen atom, $Y^j$ represents a group of formula =$CR^{5j}$—;

$R^{1j}$, $R^{2j}$, $R^{3j}$ and $R^{4j}$ each independently represents a hydrogen atom or a halogen atom;

$R^{5j}$ represents a hydrogen atom;

$R^{6j}$ represents a hydrogen atom;

$n^j$ represents 1; and

=== represents a single bond.

(6) The compound described in (1) which is 5-[6-(2-fluorobenzyloxy)-2-naphthyl-methyl]thiazolidin-2,4-dione.

Where any of the compounds of formula (I) to (X) or a pharmaceutically acceptable salt thereof can exist in the form of various isomers, for example, as stereoisomers based on an asymmetric carbon atom [for example, the carbon atom at the 2-position of the chroman ring or at the 5-position of the thiazolidine ring of compounds of formula (I) is an asymmetric carbon atom], stereoisomers based on such an asymmetric carbon atom and mixtures thereof in any ratio are all represented by the same formula. The present invention therefore embraces all of these isomers and mixtures thereof.

In each of the compounds of formula (I) to (X) and the pharmaceutically acceptable salts thereof, the 2,4-dioxothiazolidin-5-ylmethyl ring, for example, has various tautomers. In formulae (I) to (X), these tautomers and mixtures thereof in any ratio are all represented by the same formula. The present invention therefore embraces all of these isomers and mixtures thereof.

In the present invention, when any of the compounds of formulae (I) to (X) or the pharmaceutically acceptable salts thereof forms a solvate (for example a hydrate), they are also embraced by the present invention. For example, each of the compounds of formulae (I) to (X) and pharmaceutically acceptable salts thereof will form hydrates when left in the air or when recrystallized in the presence of water, and will absorb water. The present invention also embraces such solvents.

The present invention also embraces all the prodrugs, that is, compounds which are derivatives of compounds of formulas (I) to (X) and are converted under physiological conditions into the compounds of formulas (I) to (X) or into pharmaceutically acceptable salts thereof.

Preferred examples of the compounds of the present invention represented by each of formulae (I) to (X) include:

i) 5-[4-(6-hydroxy-2,5,7,8-tetramethylchroman-2-ylmethoxy)benzyl]thiazolidine-2,4-dione (troglitazone), ii) 5-[4-(6-hydroxy-2-methyl-7-t-butylchroman-2-ylmethoxy)benzyl]thiazolidine-2,4-dione, iii) 5-[4-(6-hydroxy-2-ethyl-5,7,8-trimethylchroman-2-ylmethoxy)benzyl]thiazolidine-2,4-dione, iv) 5-[4-(6-hydroxy-2-isobutyl-5,7,8-trimethylchroman-2-ylmethoxy)benzyl]thiazolidine-2,4-dione, v) 5-[4-(6-acetoxy-2,5,7,8-tetramethylchroman-2-ylmethoxy)benzyl]thiazolidine-2,4-dione, vi) 5-[4-(6-ethoxycarbonyloxy-2,5,7,8-tetramethylchroman-2-ylmethoxy)benzyl]thiazolidine-2,4-dione, vii) 5-{4-[2-(3-ethyl-2-pyridyl)ethoxy]benzyl}thiazolidine-2,4-dione, viii) 5-{4-[2-(4-ethyl-2-pyridyl)ethoxy]benzyl}thiazolidine-2,4-dione, ix) 5-{4-[2-(5-ethyl-2-pyridyl)ethoxy]benzyl}thiazolidine-2,4-dione (pioglitazone), x) 5-{4-[2-(6-ethyl-2-pyridyl)ethoxy]benzyl}thiazolidine-2,4-dione, xi) 5-[(2-benzyl-2,3-dihydrobenzofuran-5-yl)methyl]thiazolidine-2,4-dione, xii) 5-[(2-benzyl-3,4-dihydro-2H-benzopyran-6-yl)methyl]thiazolidine-2,4-dione (englitazone), xiii) 5-(4-{2-[N-methyl-N-(2-benzothiazolyl)amino]ethoxy}benzyl)thiazolidine-2,4-dione, xiv) 5-(4-{2-[N-methyl-N-(2-pyrimidinyl)amino]ethoxy}benzyl)thiazolidine-2,4-dione, xv) 5-(4-{2-[N-methyl-N-(4,5-dimethylthiazol-2-yl)amino]ethoxy}benzyl)thiazolidine-2,4-dione, xvi) 5-{4-[2-(N-methyl-N-thiazol-2-ylamino)ethoxy]benzyl}thiazolidine-2,4-dione, xvii) 5-(4-{2-[N-methyl-N-(4-phenylthiazol-2-yl)amino]ethoxy}benzyl)thiazolidine-2,4-dione, xviii) 5-(4-{2-[N-methyl-N-(4-phenyl-5-methylthiazol-2-yl)amino]ethoxy}benzyl)thiazolidine-2,4-dione, xix) 5-(4-{2-[N-methyl-N-(4-methyl-5-phenylthiazol-2-yl)amino]ethoxy}benzyl)thiazolidine-2,4-dione, xx) 5-(4-{2-[N-methyl-N-(5-phenyloxazol-2-yl)amino]ethoxy}benzyl)thiazolidine-2,4-dione, xxi) 5-(4-{2-[N-methyl-N-(4,5-dimethyloxazol-2-yl)amino]ethoxy}benzyl)thiazolidine-2,4-dione, xxii) 5-{4-[2-(2-pyrimidinylamino)ethoxy]benzyl}thiazolidine-2,4-dione,
xxiii) 5-{4-[2-(N-acetyl-N-pyrimidin-2-ylamino)ethoxy]benzyl}thiazolidine-2,4-dione,
xxiv) 5-(4-{2-[N-(2-benzothiazolyl)-N-benzylamino]ethoxy}benzyl)thiazolidine-2,4-dione,
xxv) 5-(4-{3-[N-methyl-N-(2-benzoxazolyl)amino]propoxy}benzyl)thiazolidine-2,4-dione,
xxvi) 5-{4-[2-(N-methyl-N-pyrid-2-ylamino)ethoxy]benzyl}thiazolidine-2,4-dione (rosiglitazone),
xxvii) 5-(4-{2-[1-(4-biphenylyl)ethylideneaminooxy]ethoxy}benzyl)thiazolidine-2,4-dione,
xxviii) 5-(4-{2-[1-(4-phenylsulfonylphenyl)ethylideneaminooxy]ethoxy}benzyl)thiazolidine-2,4-dione,
xxix) 5-(4-{2-[1-(4-pyrid-2'-ylphenyl)ethylideneaminooxy]ethoxy}benzyl)thiazolidine-2,4-dione (Compound A),
xxx) 5-(4-{2-[1-(4-pyrid-3'-ylphenyl)ethylideneaminooxy]ethoxy}benzyl)thiazolidine-2,4-dione,
xxxi) 5-(4-{2-[1-(4-pyrid-4'-ylphenyl)ethylideneaminooxy]ethoxy}benzyl)thiazolidine-2,4-dione,
xxxii) 5-(4-{2-[1-(2-phenyl-5-pyridyl)ethylideneaminooxy]ethoxy}benzyl)thiazolidine-2,4-dione,
xxxiii) 5-(4-{2-[1-(2-methoxy-5-pyridyl)ethylideneaminooxy]ethoxy}benzyl)thiazolidine-2,4-dione,
xxxiv) 5-(4-{2-[1-(2-ethoxy-5-pyridyl)ethylideneaminooxy]ethoxy}benzyl)thiazolidine-2,4-dione,
xxxv) 5-(4-{2-[1-(2-isopropoxy-5-pyridyl)ethylideneaminooxy]ethoxy}benzyl)thiazolidine-2,4-dione,
xxxvi) 5-(4-{2-[1-(2-benzyl-5-pyridyl)ethylideneaminooxy]ethoxy}benzyl)thiazolidine-2,4-dione,
xxxvii) 4-{4-[2-(2-phenyl-5-methyl-4-oxazolyl)ethoxy]benzyl}-3,5-isoxazolidinedione,
xxxviii) 4-{4-[2-(2-phenyl-5-methyl-4-oxazolyl)ethoxy]benzylidene}-3,5-isoxazolidinedione,
xxxix) 4-{4-[2-(2-benzothienyl-5-methyl-4-oxazolyl)ethoxy]benzyl}-3,5-isoxazolidinedione,
xl) 4-[4-(2-{5-methyl-2-[1-(2-pyridylthio)ethyl]-4-oxazolyl}ethoxy)benzyl]-3,5-isoxazolidinedione.
xli) 5-{4-(3-methylimidazo[4,5-b]pyridin-2-ylmethoxy)benzyl}thiazolidine-2,4-dione,
xlii) 5-{4-(5-chloro-3-methylimidazo[4,5-b]pyridin-2-ylmethoxy)benzyl}thiazolidine-2,4-dione,
xliii) 5-{4-(5-methoxy-3-methylimidazo[4,5-b]pyridin-2-ylmethoxy)benzyl}thiazolidine-2,4-dione,
xliv) 5-{4-(5-hydroxy-3-methylimidazo[4,5-b]pyridin-2-ylmethoxy)benzyl}thiazolidine-2,4-dione,
xlv) 5-{4-(5-ethoxy-3-methylimidazo[4,5-b]pyridin-2-ylmethoxy)benzyl}thiazolidine-2,4-dione,
xlvi) 5-{4-(5-isopropoxy-3-methylimidazo[4,5-b]pyridin-2-ylmethoxy)benzyl}thiazolidine-2,4-dione,
xlvii) 5-[4-(1-methylindolin-2-ylmethoxy)benzyl]thiazolidine-2,4-dione,
xlviii) 5-[4-(1-methylbenzimidazol-2-ylmethoxy)benzyl]thiazolidine-2,4-dione,
xlix) 5-[4-(6-methoxy-1-methylbenzimidazol-2-ylmethoxy)benzyl]thiazolidine-2,4-dione (Compound B),
l) 5-[4-(5-methoxy-1-methylbenzimidazol-2-ylmethoxy)benzyl]thiazolidine-2,4-dione,
li) 5-[4-(1-benzylbenzimidazol-5-ylmethoxy)benzyl]thiazolidine-2,4-dione,
lii) 5-[4-(5-hydroxy-1,4,6,7-tetramethylbenzimidazol-2-ylmethoxy)benzyl]thiazolidine-2,4-dione,
liii) 5-[4-(5-acetoxy-1,4,6,7-tetramethylbenzimidazol-2-ylmethoxy)benzyl]thiazolidine-2,4-dione,
liv) 5-{4-[3-(5-methyl-2-phenyloxazol-4-yl)propionyl]benzyl}thiazolidine-2,4-dione, and
lv) 5-[6-(2-fluorobenzyloxy)-2-naphthylmethyl]thiazolidine-2,4-dione;
and pharmaceutically acceptable salts thereof.

Of these, the following compounds are more preferred:
i) 5-[4-(6-hydroxy-2,5,7,8-tetramethylchroman-2-ylmethoxy)benzyl]thiazolidine-2,4-dione (troglitazone),
ii) 5-[4-(6-acetoxy-2,5,7,8-tetramethylchroman-2-ylmethoxy)benzyl]thiazolidine-2,4-dione,
iii) 5-[4-(6-ethoxycarbonyloxy-2,5,7,8-tetramethylchroman-2-ylmethoxy)benzyl]thiazolidine-2,4-dione,
iv) 5-{4-[2-(5-ethyl-2-pyridyl)ethoxy]benzyl}thiazolidine-2,4-dione (pioglitazone),
v) 5-[(2-benzyl-3,4-dihydro-2H-benzopyran-6-yl)methyl]thiazolidine-2,4-dione (englitazone),
vi) 5-{4-[2-(N-methyl-N-pyrid-2-ylamino)ethoxy]benzyl}thiazolidine-2,4-dione (rosiglitazone),
vii) 5-(4-{2-[1-(4-pyrid-2'-ylphenyl)ethylideneaminooxy]ethoxy}benzyl)thiazolidine- 2,4-dione (Compound A),
viii) 4-{4-[2-(2-phenyl-5-methyl-4-oxazolyl)ethoxy]benzyl}-3,5-isoxazolidinedione,
ix) 5-{4-(5-methoxy-3-methylimidazo[4,5-b]pyridin-2-ylmethoxy)benzyl}thiazolidine-2,4-dione,
x) 5-[4-(1-methylindolin-2-ylmethoxy)benzyl]thiazolidine-2,4-dione,
xi) 5-[4-(1-methylbenzimidazol-2-ylmethoxy)benzyl]thiazolidine-2,4-dione,
xii) 5-[4-(6-methoxy-1-methylbenzimidazol-2-ylmethoxy)benzyl]thiazolidine-2,4-dione (Compound B),
xiii) 5-[4-(5-hydroxy-1,4,6,7-tetramethylbenzimidazol-2-ylmethoxy)benzyl]thiazolidine-2,4-dione,
xiv) 5-{4-[3-(5-methyl-2-phenyloxazol-4-yl)propionyl]benzyl}thiazolidine-2,4-dione, and
xv) 5-[6-(2-fluorobenzyloxy)-2-naphthylmethyl]thiazolidine-2,4-dione;
and pharmaceutically acceptable salts thereof.

Of these, the following compounds are most preferred:
i) 5-[4-(6-hydroxy-2,5,7,8-tetrainethylchroman-2-ylmethoxy)benzyl]thiazolidine-2,4-dione (troglitazone),
ii) 5-{4-[2-(5-ethyl-2-pyridyl)ethoxy]benzyl}thiazolidine-2,4-dione (pioglitazone),
iii) 5-{4-[2-(N-methyl-N-pyrid-2-ylamino)ethoxy]benzyl}thiazolidine-2,4-dione (rosiglitazone),
iv) 5-(4-{2-[1-(4-pyrid-2'-ylphenyl)ethylideneaminooxy]ethoxy}benzyl)thiazolidine-2,4-dione (Compound A) and
v) 5-[4-(6-methoxy-1-methylbenzimidazol-2-ylmethoxy)benzyl]thiazolidine-2,4-dione (Compound B);
and pharmaceutically acceptable salts thereof.

The level of uric acid in the blood of a patient may be measured in a conventional manner. Specifically, blood is collected before and after the administration, for a predetermined period, of a medicament to a patient suffering from hyperuricemia and then the blood uric acid level is measured, for example, by the uricase catalase method [Kageyama: Clin. Chim. Acta., 31, 421–426 (1971)]. A measuring kit employing the above method is commercially available ("Uricolor 400", trade name; product of Ono Pharmaceutical Co., Ltd.)

The insulin sensitivity enhancer to be used in the present invention may be administered in various forms. There is no particular limitation on the administration form, which will be determined depending on the formulation, as well as on the age, sex or other condition of a patient and/or the severity of the disease. For example, for oral administration, the compound may be employed in the form of a tablet, pill, powder, granule, syrup, solution, suspension, emulsion or capsule. For intravenous administration, the compound may be employed in the form of an injection, with or without a commonly used supplement, such as glucose or amino acid. It can be administered alone intramuscularly, intracutaneously, subcutaneously or intraperitoneally, if necessary. It can also be administered intrarectally as a suppository. Oral administration is generally preferred.

The various preparations described above can be formulated using known adjuvants which are normally employed in this field, such as excipients, binders, disintegrating agents, lubricants, solubilizing agents, corrigents, coating agents and the like.

For the formulation of a tablet, various carriers which are conventionally known in this field can be used. Examples include: excipients, such as lactose, saccharose, sodium chloride, glucose, urea, starch, calcium carbonate, kaolin, crystalline cellulose and silicic acid; binders, such as water, ethanol, propanol, simple syrup, glucose solution, starch solution, gelatin solution, carboxymethyl cellulose, shellac, methyl cellulose, potassium phosphate and polyvinyl pyrrolidone sugar; disintegrating agents, such as dry starch, sodium alginate, agar powder, laminaran powder, sodium bicarbonate, calcium carbonate, polyoxyethylene sorbitan fatty acid esters, sodium lauryl sulfate, stearic monoglyceride, starch and lactose; disintegration suppressants, such as saccharose, stearin, cacao butter and hydrogenated oil; absorption facilitators, such as quaternary ammonium bases and sodium lauryl sulfate; humectants, such as glycerin and starch, adsorbents, such as starch, lactose, kaolin, bentonite and colloid silicic acid; and lubricants, such as purified talc, stearate, boric acid powder and polyethylene glycol. If necessary, the tablet can be coated, for example sugar-coated, gelatin-coated, enteric-coated or film-coated; the tablet can be formed as a double-layer or multi-layer tablet.

For the formation of a pill, various carriers known in this field can be used. Examples include excipients, such as glucose, lactose, starch, cacao oil, hydrogenated vegetable oil, kaolin and talc; binders, such as gum arabic powder, tragacanth powder, gelatin and ethanol; and disintegrating agents, such as laminaran agar.

For the formation of a suppository, various carriers which are conventionally known in this field can be used. Examples include polyethylene glycol, cacao oil, higher alcohols, esters of higher alcohols, gelatin and semi-synthetic glyceride.

When formulated as an injection, a sterilized solution or suspension which is isotonic with the blood is preferred. For the formation of a solution, emulsion or suspension, any diluent that is conventionally used in this field can be used. Examples include water, ethyl alcohol, propylene glycol, ethoxylated isostearyl alcohol, polyoxylated isostearyl alcohol and polyoxyethylene sorbitan fatty acid ester. In this case, it is possible to include sodium chloride, glucose or glycerin in an amount sufficient to prepare an isotonic solution or to add a conventional adjuvant for solubilization, buffering agent, soothing agent and the like. Furthermore, a colorant, preservative, aroma chemical, flavoring agent, sweetening agent and/or another medicament may be added if necessary.

There is no particular limitation on the amount of active compound to be incorporated in the above pharmaceutical preparation. The amount may be selected freely as needed, but we generally prefer to incorporate the compound in an amount of from 1 to 70% by weight, preferably from 1 to 30% by weight based on the whole composition.

The dosage of the insulin sensitivity enhancer may vary, depending on the symptoms, age, body weight and condition of the patient, as well as upon the route of administration and the like. In the case of oral administration, it is desirable to administer to an adult human patient at least 0.1 mg (preferably 1 mg) and preferably no more than 1000 mg (preferably 500 mg) per day, depending on the symptoms, which may be administered in a single dose or in divided doses. In the case of intravenous administration, an amount of 0.01 mg (preferably 0.1 mg) as a lower limit and 500 mg (preferably 200 mg) as an upper limit per adult per day is desirable, depending on the symptoms, which may be administered in a single dose or in divided doses.

The invention will be described in more detail by the following Example, which illustrates the activity of the compounds of the present invention, and the subsequent Formulation Examples.

EXAMPLE

Improvement in Hyperuricemia (H.U.)

4 adult human patients who had suffered from diabetes and hyperuricemia and whose blood uric acid level was not less than 7.0 mg/dl, were administered orally 200 mg of troglitazone twice a day (in the morning and in the evening). This administration was continued for 4 weeks. Both after and before administration, blood was collected and the blood uric acid level was measured.

The results are shown in the following Table.

| Patient | Medical history of gout including complications | Concomitant use of another remedy for H.U. | Blood uric acid level (mg/dl) | |
| --- | --- | --- | --- | --- |
| | | | Week 0 | Week 4 |
| 1 (male) | None | None | 7.2 | 5.2 |
| 2 (male) | None | None | 7.6 | 5.3 |
| 3 (female) | None | None | 7.9 | 5.6 |
| 4 (male) | None | None | 7.2 | 5.2 |

As is apparent from the above Table, the administration of troglitazone to patients suffering from hyperuricemia, having a blood uric acid level as high as 7.0 mg/dl or greater, results in the blood uric acid level being reduced to 6.0 mg/dl or less which is in the normal range.

Test

Acute Toxicity

The acute toxicity of troglitazone was measured in a conventional manner. Specifically, 300 mg/kg of troglitazone was administered orally to three ddY mice (male), which were then observed for 5 days. All of them survived.

Formulation Example 1

Powders

Powders can be obtained by mixing 5 g of troglitazone, 895 g of lactose and 100 g of corn starch in a blender.

Formulation Example 2

Granules

Granules can be obtained by mixing 5 g of troglitazone, 865 g of lactose and 100 g of low-substituted hydroxypropyl cellulose, adding to the mixture 300 g of a 10% w/v aqueous solution of hydroxypropyl cellulose, kneading the resulting mixture, granulating the kneaded mass using an extrusion granulator and then drying the granulated product.

Formulation Example 3

Capsules

Capsules can be obtained by mixing 5 g of troglitazone, 115 g of lactose, 58 g of corn starch and 2 g of magnesium stearate in a V-shaped mixer and then filling the resulting mixture, in 180 mg portions, into No.3 capsules.

Formulation Example 4

Tablets

Tablets can be obtained by mixing 5 g of troglitazone, 90 g of lactose, 34 g of corn starch, 20 g of crystalline cellulose and 1 g of magnesium stearate in a blender and then tableting the resulting mixture by a tableting machine.

Formulation Example 5

Powders

Powders can be obtained by mixing 5 g of pioglitazone, 895 g of lactose and 100 g of corn starch in a blender.

Formulation Example 6

Granules

Granules can be prepared by mixing 5 g of rosiglitazone, 865 g of lactose and 100 g of low-substituted hydroxypropyl cellulose, adding to the mixture 300 g of a 10% w/v aqueous solution of hydroxypropyl cellulose, kneading the resulting mixture, granulating the kneaded mass using an extrusion granulator and then drying the granulated product.

Formulation Example 7

Capsules

Capsules can be obtained by mixing 5 g of Compound A, 115 g of lactose, 58 g of corn starch and 2 g of magnesium stearate in a V-shaped mixer and then filling the resulting mixture, in 180 mg portions, into No.3 capsules.

Formulation Example 8

Tablets

Tablets can be obtained by mixing 5 g of Compound A, 90 g of lactose, 34 g of corn starch, 20 g of crystalline cellulose and 1 g of magnesium stearate in a blender and then tableting the resulting mixture by a tableting machine.

What is claimed is:

1. A method for the treatment or prevention of hyperuricemia in a human in need thereof, which comprises administering to said human an amount of an insulin sensitivity enhancer effective to reduce or prevent hyperuricemia.

2. The method of claim 1, wherein said insulin sensitivity enhancer is selected from the group consisting of thiazolidinedione compounds, iminothiazolidinone compounds, diiminothiazolidine compounds, thioxothiazolidinone compounds, iminotriazole compounds, oxazolidinedione compounds, isoxazolidinedione compounds and oxadiazolidinedione compounds.

3. The method of claim 1, wherein said insulin sensitivity enhancer is selected from the group consisting of thiazolidinedione compounds, iminothiazolidinone compounds, and diiminothiazolidine compounds.

4. The method of claim 1, wherein said insulin sensitivity enhancer is selected from the group consisting of thiazolidinedione compounds.

5. The method of claim 1, wherein said insulin sensitivity enhancer is selected from the group consisting of compounds of formula (I):

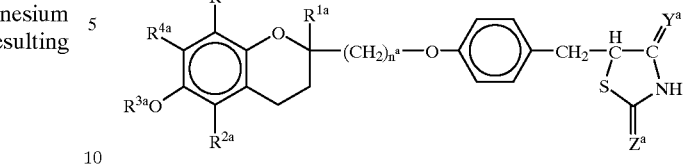

(I)

wherein:
- $R^{1a}$ and $R^{2a}$ are the same or different and each represents a hydrogen atom or an alkyl group having from 1 to 5 carbon atoms;
- $R^{3a}$ represents a hydrogen atom, an aliphatic acyl group having from 1 to 6 carbon atoms, a cycloalkylcarbonyl group having from 6 to 8 carbon atoms, a benzoyl or naphthoyl group which is unsubstituted or is substituted by at least one substituent selected from the group consisting of substituents $\chi$, defined below, a heterocyclic acyl group in which the heterocyclic part has from 4 to 7 ring atoms of which from 1 to 3 are hetero-atoms selected from the group consisting of nitrogen, oxygen and sulfur atoms, a phenylacetyl group, a phenylpropionyl group, a phenylacetyl or phenylpropionyl group substituted with at least one halogen atom, a cinnamoyl group, an alkoxycarbonyl group having from 2 to 7 carbon atoms or a benzyloxycarbonyl group;
  - said substituent $\chi$ is an alkyl group having from 1 to 4 carbon atoms, an alkoxy group having from 1 to 4 carbon atoms, a hydroxy group, a halogen atom, an amino group, a monoalkylamino group having from 1 to 4 carbon atoms, a dialkylamino group having from 1 to 4 carbon atoms in each alkyl group or a nitro group;
- $R^{4a}$ and $R^{5a}$ are the same or different and each represents a hydrogen atom, an alkyl group having from 1 to 5 carbon atoms or an alkoxy group having from 1 to 5 carbon atoms, or $R^{4a}$ and $R^{5a}$ together represent an alkylenedioxy group having from 1 to 4 carbon atoms;
- $Y^a$ and $Z^a$ are the same or different and each represents an oxygen atom or an imino group; and
- $n^a$ represents an integer of from 1 to 3;

and pharmaceutically acceptable salts thereof.

6. The method of claim 1, wherein said insulin sensitivity enhancer is selected from the group consisting of compounds of formula (II):

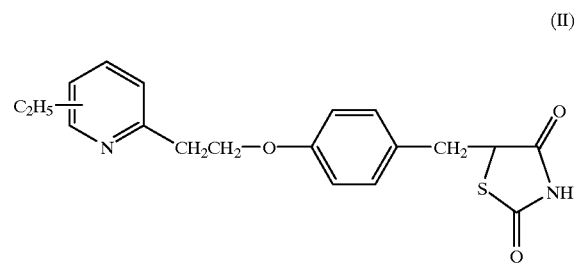

(II)

and pharmaceutically acceptable salts thereof.

7. The method of claim 1, wherein said insulin sensitivity enhancer is selected from the group consisting of compounds of formula (III):

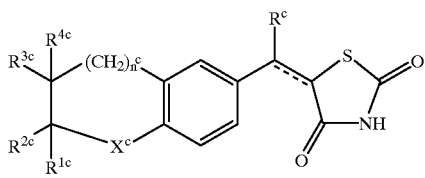

(III)

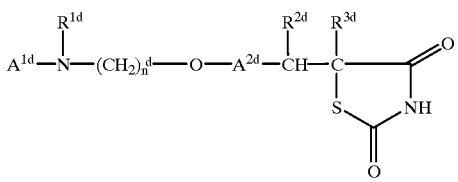

(IV)

wherein:

==== represents a single or double bond;

$n^c$ represents 0, 1 or 2;

$X^c$ represents an oxygen atom, a sulfur atom, a sulfinyl group or a sulfonyl group;

$R^c$ represents a hydrogen atom, a methyl group or an ethyl group;

$R^{1c}$ represents a cycloalkyl group having from 5 to 7 carbon atoms, a cycloalkyl group having from 5 to 7 carbon atoms and substituted by a methyl group, a pyridyl group, a thienyl group, a furyl group, a naphthyl group, a p-biphenylyl group, a tetrahydrofuranyl group, a tetrahydrothienyl group, a tetrahydropyranyl group, a group of formula $C_6H_4W^{2c}$ wherein $W^{2c}$ represents a hydrogen atom, a hydroxy group, a halogen atom, an alkyl group having from 1 to 4 carbon atoms, an alkoxy group having from 1 to 4 carbon atoms or an alkylthio group having from 1 to 4 carbon atoms or a group of formula alk-$W^{1c}$ wherein alk represents an alkylene group having from 1 to 6 carbon atoms, an ethylidene group or an isopropylidene group and $W^{1c}$ represents a hydrogen atom, a hydroxy group, an alkoxy group having from 1 to 4 carbon atoms, an alkylthio group having from 1 to 4 carbon atoms, a pyridyl group, a furyl group, a thienyl group, a tetrahydrofuryl group, a tetrahydrothienyl group, a naphthyl group, a cycloalkyl group having from 5 to 7 carbon atoms or a group of formula $C_6H_4W^{2c}$, where $W^{2c}$ is as defined above;

$R^{2c}$ represents a hydrogen atom or a methyl group;

$R^{3c}$ represents a hydrogen atom, an alkyl group having from 1 to 6 carbon atoms, a group of formula $C_6H_4W^{2c}$ where $W^{2c}$ is as defined above or a benzyl group;

$R^{4c}$ represents a hydrogen atom, or $R^{1c}$ and $R^{2c}$ together form an alkylene group having from 4 to 6 carbon atoms, and $R^{3c}$ and $R^{4c}$ both represent hydrogen atoms; or $R^{3c}$ and $R^{4c}$ together form an alkylene group having from 4 to 6 carbon atoms, and $R^{1c}$ and $R^{2c}$ both represent hydrogen atoms; or $R^{2c}$ and $R^{3c}$ together form an alkylene group having from 3 or 4 carbon atoms, and $R^{1c}$ and $R^{4c}$ both represent hydrogen atoms;

and pharmaceutically acceptable salts thereof.

8. The method of claim 1, wherein said insulin sensitivity enhancer is selected from the group consisting of compounds of formula (IV):

wherein:

$A^{1d}$ represents a substituted or unsubstituted aromatic heterocyclic group, $R^{1d}$ represents a hydrogen atom, an alkyl group, an acyl group, an aralkyl group (the aryl moiety of said aralkyl group may be substituted or unsubstituted) or a substituted or unsubstituted aryl group, $R^{2d}$ and $R^{3d}$ each represents a hydrogen atom or together form a bond, $A^{2d}$ represents a benzene ring which has at most a total of 5 substituents; and $n^d$ represents an integer of from 2 to 6;

and pharmaceutically acceptable salts thereof.

9. The method of claim 1, wherein said insulin sensitivity enhancer is selected from the group consisting of compounds of formula (V):

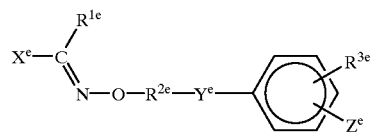

(V)

wherein:

$R^{1e}$ represents a hydrogen atom or a straight or branched chain alkyl group having from 1 to 6 carbon atoms, $R^{2e}$ represents a straight or branched chain alkylene group having from 2 to 6 carbon atoms, $R^{3e}$ represents a hydrogen atom, a straight or branched chain alkyl group having from 1 to 6 carbon atoms, a straight or branched chain alkoxy group having from 1 to 4 carbon atoms, a straight or branched chain alkylthio group having from 1 to 4 carbon atoms, a halogen atom, a nitro group, an amino group, a straight or branched chain monoalkylamino group having from 1 to 4 carbon atoms, a straight or branched chain dialkylamino group in which each alkyl group has from 1 to 4 carbon atoms, an aryl group having from 6 to 10 carbon atoms or an aralkyl group having from 7 to 12 carbon atoms, $X^e$ represents an aryl group having from 6 to 10 carbon atoms which is unsubstituted or is substituted by from 1 to 3 of substituents α, defined below, or a heteroaromatic group which is unsubstituted or is substituted by from 1 to 3 of substituents α, defined below, said substituents α each representing (i) a straight or branched chain alkyl group having from 1 to 6 carbon atoms, (ii) a straight or branched chain haloalkyl group having from 1 to 4 carbon atoms, (iii) a hydroxy group, (iv) a straight or branched chain acyloxy group having from 1 to 4 carbon atoms, (v) a straight or branched chain alkoxy group having from 1 to 4 carbon atoms, (vi) a straight or branched chain alkylenedioxy group having from 1 to 4 carbon atoms, (vii) an aralkyloxy group having from 7 to 12 carbon atoms, (viii) a straight or branched chain alkylthio group having from 1 to 4 carbon atoms, (ix) a straight or branched chain alkylsulfonyl group having from 1 to 4 carbon atoms, (x) a halogen atom, (xi) a nitro group, (xii) an amino group, (xiii) a straight or branched chain monoalkylamino group having from 1 to 4 carbon atoms, (xiv) a straight or branched chain dialkylamino group in which each alkyl group has from 1 to 4 carbon atoms, (xv) an aralkyl group having from 7 to 12 carbon atoms, (xvi) an aryl group having from 6 to 10 carbon atoms which is unsubstituted or is substituted by at least one substituent selected from the group consisting of substituents β, defined below, (xvii) an aryloxy group having from 6 to 10 carbon atoms which is unsubstituted or is substituted by at least one substituent selected from the group consisting of substituents β, defined below, (xviii) an arylthio group having from 6 to 10 carbon atoms which is unsubstituted or is substituted by at least one substituent selected from the group consisting of substituents β, defined below, (xix) an arylsulfonyl group having from 6 to 10 carbon atoms which is unsubstituted or is substituted by at least one substituent selected from the group consisting of substituents β, defined below, (xx) an arylsulfonylamino group having from 6 to 10 carbon atoms which is unsubstituted or is substituted by at least one substituent selected from the group consisting of substituents β, defined below, and in which the nitrogen atom of the amino moiety is unsubstituted or is substituted by a straight or branched chain alkyl group having from 1 to 6 carbon atoms, (xxi) a heteroaromatic group, (xxii) a heteroaryloxy group, (xxiii) a heteroarylthio group, (xxiv) a heteroarylsulfonyl group or (xxv) a heteroaromatic sulfonylamino group in which the nitrogen atom of the amino moiety is unsubstituted or is substituted by a straight or branched chain alkyl group having from 1 to 6 carbon atoms;

said substituent β representing a straight or branched chain alkyl group having from 1 to 6 carbon atoms, a straight or branched chain haloalkyl group having from 1 to 4 carbon atoms, a straight or branched chain alkoxy group having from 1 to 4 carbon atoms, a halogen atom or a straight or branched chain alkylenedioxy group having from 1 to 4 carbon atoms;

$Y^e$ represents an oxygen atom, a sulfur atom or group of formula $>N-R^{4e}$
wherein $R^{4e}$ represents a hydrogen atom, a straight or branched chain alkyl group having from 1 to 6 carbon atoms or a straight or branched chain acyl group having from 1 to 8 carbon atoms; and $Z^e$ represents a 2,4-dioxothiazolidin-5-ylidenylmethyl, 2,4-dioxothiazolidin-5-ylmethyl, 2,4-dioxooxazolidin-5-ylmethyl or 3,5-dioxooxadiazolidin-2-ylmethyl group;

and pharmaceutically acceptable salts thereof.

10. The method of claim 1, wherein said insulin sensitivity enhancer is selected from the group consisting of compounds of formula (VI):

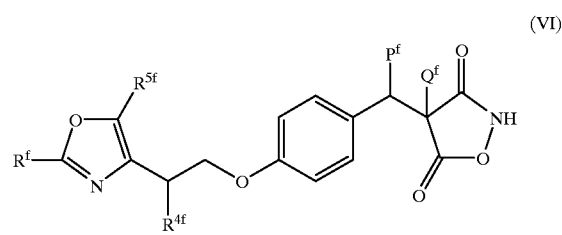

(VI)

wherein:
$R^f$ represents an aromatic hydrocarbon group which may be substituted, a cyclic aliphatic hydrocarbon group which may be substituted, a heterocyclic group which may be substituted, a fused heterocyclic group which may be substituted or a group of formula (VIa):

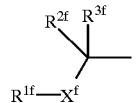

(VIa)

wherein $R^{1f}$ represents an aromatic hydrocarbon group which may be substituted, a cyclic aliphatic hydrocarbon group which may be substituted, a heterocyclic group which may be substituted or a fused heterocyclic group which may be substituted, $R^{2f}$ and $R^{3f}$ are the same or different and each represents a hydrogen atom or a lower alkyl group, $X^f$ represents an oxygen atom, a sulfur atom or a secondary amino group;

$R^{4f}$ represents a hydrogen atom or a lower alkyl group;

$R^{5f}$ represents a lower alkyl group;

$P^f$ and $Q^f$ each represents a hydrogen atom or together form a bond;

and pharmaceutically acceptable salts thereof.

11. The method of claim 1, wherein said insulin sensitivity enhancer is selected from the group consisting of compounds of formula (VII):

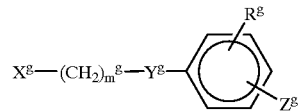

(VII)

wherein:
$X^g$ represents an indole, indoline, azaindole, azaindoline, imidazopyridine or imidazopyrimidine ring group which is unsubstituted or is substituted by from 1 to 3 substituents selected from the group consisting of substituents δ, defined below;

$Y^g$ represents an oxygen or sulfur atom;

$Z^g$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethyl group;

$R^g$ represents a hydrogen atom, a straight or branched chain alkyl group having from 1 to 4 carbon atoms, a straight or branched chain alkoxy group having from 1 to 4 carbon atoms, a halogen atom, a hydroxy group, a nitro group, an amino group which is unsubstituted or is substituted by at least one substituent selected from the group consisting of substituents ε, defined below, or a straight or branched chain aralkyl group having from 7 to 11 carbon atoms;

said substituent s represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, an aromatic aliphatic acyl group having from 8 to 12 carbon atoms or an aromatic acyl group having from 7 to 11 carbon atoms; and $m^g$ represents an integer of from 1 to 5, said substituent δ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents ε, defined above, an aryl group having from 6 to 10 carbon atoms which is unsubstituted or is substituted by at least one substituent selected from the group consisting of substituents φ, or a straight or branched chain aralkyl group having from 7 to 11 carbon atoms which is unsubstituted or is substituted by at least one substituent selected from the group consisting of substituents φ, said substituent φ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents ε, defined above;

and pharmaceutically acceptable salts thereof.

12. The method of claim 1, wherein said insulin sensitivity enhancer is selected from the group consisting of compounds of formula (VII):

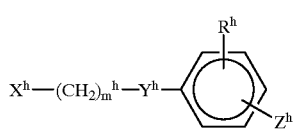

(VIII)

wherein:

$X^h$ represents a benzimidazole ring group which is unsubstituted or is substituted by from 1 to 5 substituents selected from the group consisting of substituents γ, defined below, $Y^h$ represents an oxygen or sulfur atom, $Z^h$ represents a 2,4-dioxothiazolidin-5-ylidenylmethyl, 2,4-dioxothiazolidin-5-ylmethyl, 2,4-dioxooxazolidin-5-ylmethyl, 3,5-dioxooxadiazolidin-2-ylmethyl or N-hydroxyureidomethyl group;

$R^h$ represents a hydrogen atom, a straight or branched chain alkyl group having from 1 to 4 carbon atoms, a straight or branched chain alkoxy group having from 1 to 4 carbon atoms, a halogen atom, a hydroxy group, a nitro group, an amino group which is unsubstituted or is substituted by at least one substituent selected from the group consisting of substituents η, defined below, or a straight or branched chain aralkyl group having from 7 to 11 carbon atoms, and $m^h$ represents an integer of from 1 to 5, said substituent γ represents a straight or branched chain alkyl group having from 1 to 4 carbon atoms, a straight or branched chain alkoxy group having from 1 to 4 carbon atoms, a benzyloxy group, a halogen atom, a hydroxy group, an acetoxy group, a phenylthio group, a straight or branched chain alkylthio group having from 1 to 4 carbon atoms, a trifluoromethyl group, a nitro group, an amino group which is unsubstituted or is substituted by at least one substituent selected from the group consisting of substituents η, defined below, an aryl group having from 6 to 10 carbon atoms which is unsubstituted or is substituted by at least one substituent selected from the group consisting of substituents λ, defined below, or a straight or branched chain aralkyl group having from 7 to 11 carbon atoms which is unsubstituted or is substituted by at least one substituent selected from the group consisting of substituents λ, defined below;

said substituent η represents a straight or branched chain alkyl group having from 1 to 8 carbon atoms, a straight or branched chain aralkyl group having from 7 to 11 carbon atoms, an aryl group having from 6 to 10 carbon atoms, a straight or branched chain aliphatic acyl group having from 1 to 11 carbon atoms, a aromatic aliphatic acyl group having from 8 to 12 carbon atoms or an aromatic acyl group having from 7 to 11 carbon atoms.

said substituent λ represents a straight or branched chain alkyl group having from 1 to 4 carbon atoms, a straight or branched chain alkoxy group having from 1 to 4 carbon atoms, a halogen atom, a hydroxy group, a nitro group, a phenyl group, a trifluoromethyl group or an amino group which is unsubstituted or is substituted by at least one substituent selected from the group consisting of substituents η, defined above;

and pharmaceutically acceptable salts thereof.

13. The method of claim 1, wherein said insulin sensitivity enhancer is selected from the group consisting of compounds of formula (IX):

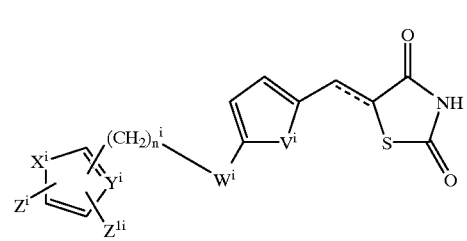

(IX)

wherein:

=== represents a single or double bond;

$V^i$ represents a group of formula —CH═CH—, —N═CH— or —CH═N— or a sulfur atom;

$W^i$ represents a group of formula >CH$_2$, >CHOH, >CO, >C═NOR$^i$ or —CH═CH—, $X^i$ represents a sulfur or oxygen atom or a group of formula >NR$^{1i}$, —CH═N— or —N═CH—, $Y^i$ represents a group of formula ═CH— or a nitrogen atom, $Z^i$ represents a hydrogen atom, an alkyl group having from 1 to 7 carbon atoms, a cycloalkyl group having from 3 to 7 carbon atoms, a phenyl group, a naphthyl group, a pyridyl group, a furyl group, a thienyl group or a phenyl group substituted with one or two substituents selected from the group consisting of alkyl groups having from 1 to 3 carbon atoms, trifluoromethyl groups, alkoxy groups having from 1 to 3 carbon atoms, fluorine atoms, chlorine atoms and bromine atoms, $Z^{1i}$ represents a hydrogen atom or an alkyl group having from 1 to 3 carbon atoms, $R^i$ and $R^{1i}$ each independently represents a hydrogen atom or a methyl group, and $n^i$ represents 1, 2 or 3;

and pharmaceutically acceptable salts thereof.

14. The method of claim 1, wherein said insulin sensitivity enhancer is selected from the group consisting of compounds of formula (X):

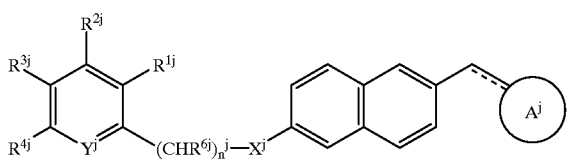

(X)

wherein:

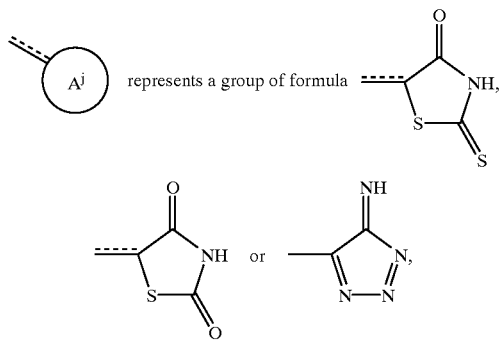

—$X^j$— represents an oxygen or sulfur atom;

=$Y^j$— represents =N— or a group of formula =$CR^{5j}$—;

$R^{1j}$, $R^{2j}$, $R^{3j}$, $R^{4j}$ and $R^{5j}$ each independently represents a hydrogen atom, a halogen atom, an alkyl group, an aryl group, an alkoxy group, an alkoxyalkoxy group, an aryloxy group, an alkanoyloxy group, an arylcarbonyloxy group, a carboxyl group, an alkoxycarbonyl group, an aryloxycarbonyl group, a carbamoyl group, an alkylaminocarbonyl group, an arylaminocarbonyl group, an amino group, an alkylamino group, an alkanoylamino group, an arylcarbonylamino group, an ethylenedioxymethyl group, a formyl group, a cyano group, a nitro group or a trihalomethyl group, $R^{6j}$ represents a hydrogen atom, an alkyl group which may be substituted or an aryl group which may be substituted, and $n^j$ represents 0 or an integer of from 1 to 3;

and === may represent a single or double bond;

and pharmaceutically acceptable salts thereof.

15. The method of claim 1, wherein said insulin sensitivity enhancer is selected from the group consisting of:

i) 5-[4-(6-hydroxy-2,5,7,8-tetramethylchroman-2-ylmethoxy)benzyl]thiazolidine-2,4-dione,
ii) 5-[4-(6-hydroxy-2-methyl-7-t-butylchroman-2-yhnethoxy)benzyl]thiazolidine-2,4-dione,
iii) 5-[4-(6-hydroxy-2-ethyl-5,7,8-trimethylchroman-2-ylmethoxy)benzyl]thiazolidine-2,4-dione,
iv) 5-[4-(6-hydroxy-2-isobutyl-5,7,8-trimethylchroman-2-ylmethoxy)benzyl]thiazolidine-2,4-dione,
v) 5-[4-(6-acetoxy-2,5,7,8-tetramethylchroman-2-ylmethoxy)benzyl]thiazolidine-2,4-dione,
vi) 5-[4-(6-ethoxycarbonyloxy-2,5,7,8-tetramethylchroman-2-ylmethoxy)benzyl]thiazolidine-2,4-dione,
vii) 5-{4-[2-(3-ethyl-2-pyridyl)ethoxy]benzyl}thiazolidine-2,4-dione,
viii) 5-{4-[2-(4-ethyl-2-pyridyl)ethoxy]benzyl}thiazolidine-2,4-dione,
ix) 5-{4-[2-(5-ethyl-2-pyridyl)ethoxy]benzyl}thiazolidine-2,4-dione,
x) 5-{4-[2-(6-ethyl-2-pyridyl)ethoxy]benzyl}thiazolidine-2,4-dione,
xi) 5-[(2-benzyl-2,3-dihydrobenzofuran-5-yl)methyl]thiazolidine-2,4-dione,
xii) 5-[(2-benzyl-3,4-dihydro-2H-benzopyran-6-yl)methyl]thiazolidine-2,4-dione,
xiii) 5-(4-{2-[N-methyl-N-(2-benzothiazolyl)amino]ethoxy}benzyl)thiazolidine-2,4-dione,
xiv) 5-(4-{2-[N-methyl-N-(2-pyrimidinyl)amino]ethoxy}benzyl)thiazolidine-2,4-dione,
xv) 5-(4-{2-[N-methyl-N-(4,5-dimethylthiazol-2-yl)amino]ethoxy}benzyl)thiazolidine-2,4-dione,
xvi) 5-{4-[2-(N-methyl-N-thiazol-2-ylamino)ethoxy]benzyl}thiazolidine-2,4-dione,
xvii) 5-(4-{2-[N-methyl-N-(4-phenylthiazol-2-yl)amino]ethoxy}benzyl)thiazolidine-2,4-dione,
xviii) 5-(4-{2-[N-methyl-N-(4-phenyl-5-methylthiazol-2-yl)amino]ethoxy}benzyl)thiazolidine-2,4-dione,
xix) 5-(4-{2-[N-methyl-N-(4-methyl-5-phenylthiazol-2-yl)amino]ethoxy}benzyl)thiazolidine-2,4-dione,
xx) 5-(4-{2-[N-methyl-N-(5-phenyloxazol-2-yl)amino]ethoxy}benzyl)thiazolidine-2,4-dione,
xxi) 5-(4-{2-[N-methyl-N-(4,5-dimethyloxazol-2-yl)amino]ethoxy}benzyl)thiazolidine-2,4-dione,
xxii) 5-{4-[2-(2-pyrimidinylamino)ethoxy]benzyl}thiazolidine-2,4-dione,
xxiii) 5-{4-[2-(N-acetyl-N-pyrimidin-2-ylamino)ethoxy]benzyl}thiazolidine-2,4-dione,
xxiv) 5-(4-{2-[N-(2-benzothiazolyl)-N-benzylamino]ethoxy}benzyl)thiazolidine-2,4-dione,
xxv) 5-(4-{3-[N-methyl-N-(2-benzoxazolyl)amino]propoxy}benzyl)thiazolidine-2,4-dione,
xxvi) 5-{4-[2-(N-methyl-N-pyrid-2-ylamino)ethoxy]benzyl}thiazolidine-2,4-dione,
xxvii) 5-(4-{2-[1-(4-biphenylyl)ethylideneaminooxy]ethoxy}benzyl)thiazolidine-2,4-dione,
xxviii) 5-(4-{2-[1-(4-phenylsulfonylphenyl)ethylideneaminooxy]ethoxy}benzyl)thiazolidine-2,4-dione,
xxix) 5-(4-{2-[1-(4-pyrid-2'-ylphenyl)ethylideneaminooxy]ethoxy}benzyl)thiazolidine-2,4-dione,
xxx) 5-(4-{2-[1-(4-pyrid-3'-ylphenyl)ethylideneaminooxy]ethoxy}benzyl)thiazolidine-2,4-dione,
xxxi) 5-(4-{2-[1-(4-pyrid-4'-ylphenyl)ethylideneaminooxy]ethoxy}benzyl)thiazolidine-2,4-dione,
xxxii) 5-(4-{2-[1-(2-phenyl-5-pyridyl)ethylideneaminooxy]ethoxy}benzyl)thiazolidine-2,4-dione,
xxxiii) 5-(4-{2-[1-(2-methoxy-5-pyridyl)ethylideneaminooxy]ethoxy}benzyl)thiazolidine-2,4-dione, xxxiv) 5-(4-{2-[1-(2-ethoxy-5-pyridyl)ethylideneaminooxy]ethoxy}benzyl)thiazolidine-2,4-dione, xxxv) 5-(4-{2-[1-(2-isopropoxy-5-pyridyl)ethylideneaminooxy]ethoxy}benzyl)thiazolidine-2,4-dione, xxxvi) 5-(4-{2-[1-(2-benzyl-5-pyridyl)ethylideneaminooxy]ethoxy}benzyl)thiazolidine-2,4-dione, xxxvii) 4-{4-[2-(2-phenyl-5-methyl-4-oxazolyl)ethoxy]benzyl}-3,5-isoxazolidinedione, xxxviii) 4-{4-[2-(2-phenyl-5-methyl-4-oxazolyl)ethoxy]benzylidene}-3,5-isoxazolidinedione, xxxix) 4-{4-[2-(2-benzothienyl-5-methyl-4-oxazolyl)ethoxy]benzyl}-3,5-isoxazolidinedione, xl) 4-[4-(2-{5-methyl-2-[1-(2-pyridylthio)ethyl]-4-oxazolyl}ethoxy)benzyl]-3,5-isoxazolidinedione, xli) 5-{4-(3-methylimidazo[4,5-b]pyridin-2-ylmethoxy)benzyl}thiazolidine-2,4-dione, xlii) 5-{4-(5-chloro-3-methylimidazo[4,5-b]pyridin-2-ylmethoxy)benzyl}thiazolidine-2,4-dione, xliii) 5-{4-(5-methoxy-3-methylimidazo[4,5-b]pyridin-2-ylmethoxy)benzyl}thiazolidine-2,4-dione, xliv) 5-{4-(5-hydroxy-3-methylimidazo[4,5-b]pyridin-2-ylmethoxy)benzyl}thiazolidine-2,4-dione, xlv) 5-{4-(5-ethoxy-3-methylimidazo[4,5-b]pyridin-2-ylmethoxy)benzyl}thiazolidine-2,4-dione, xlvi) 5-{4-(5-isopropoxy-3-methylimidazo[4,5-b]pyridin-2-ylmethoxy)benzyl}thiazolidine-2,4-dione, xlvii) 5-[4-(1-methylindolin-2-ylmethoxy)benzyl]thiazolidine-2,4-dione, xlviii) 5-[4-(1-methylbenzimidazol-2-ylmethoxy)benzyl]thiazolidine-2,4-dione, xlix) 5-[4-(6-methoxy-1-methylbenzimidazol-2-ylmethoxy)benzyl]thiazolidine-2,4-dione, l) 5-[4-(5-methoxy-1-methylbenzimidazol-2-ylmethoxy)benzyl]thiazolidine-2,4-dione, li) 5-[4-(1-benzylbenzimidazol-5-ylmethoxy)benzyl]thiazolidine-2,4-dione, lii) 5-[4-(5-hydroxy-1,4,6,7-tetramethylbenzimidazol-2-ylmethoxy)benzyl]thiazolidine-2,4-dione, liii) 5-[4-(5-acetoxy-1,4,6,7-tetramethylbenzimidazol-2-ylmethoxy)benzyl]thiazolidine-2,4-dione, liv) 5-{4-[3-(5-methyl-2-phenyloxazol-4-yl)propionyl]benzyl}thiazolidine-2,4-dione, and lv) 5-[6-(2-fluorobenzyloxy)-2-naphthylmethyl]thiazolidine-2,4-dione;

and pharmaceutically acceptable salts thereof.

16. The method of claim 1, wherein said insulin sensitivity enhancer is selected from the group consisting of:

i) 5-[4-(6-hydroxy-2,5,7,8-tetramethylchroman-2-ylmethoxy)benzyl]thiazolidine-2,4-dione), ii) 5-[4-(6-acetoxy-2,5,7,8-tetramethylchroman-2-ylmethoxy)benzyl]thiazolidine-2,4-dione, iii) 5-[4-(6-ethoxycarbonyloxy-2,5,7,8-tetramethylchroman-2-ylmethoxy)benzyl]thiazolidine-2,4-dione, iv) 5-{4-[2-(5-ethyl-2-pyridyl)ethoxy]benzyl}thiazolidine-2,4-dione, v) 5-[(2-benzyl-3,4-dihydro-2H-benzopyran-6-yl)methyl]thiazolidine-2,4-dione, vi) 5-{4-[2-(N-methyl-N-pyrid-2-ylamino)ethoxy]benzyl}thiazolidine-2,4-dione, vii) 5-(4-{2-[1-(4-pyrid-2'-ylphenyl)ethylideneaminooxy]ethoxy}benzyl)thiazolidine-2,4-dione, viii) 4-{4-[2-(2-phenyl-5-methyl-4-oxazolyl)ethoxy]benzyl}-3,5-isoxazolidinedione, ix) 5-{4-(5-methoxy-3-methylimidazo[4,5-b]pyridin-2-ylmethoxy)benzyl}thiazolidine-2,4-dione, x) 5-[4-(1-methylindolin-2-ylmethoxy)benzyl]thiazolidine-2,4-dione, xi) 5-[4-(1-methylbenzimidazol-2-ylmethoxy)benzyl]thiazolidine-2,4-dione, xii) 5-[4-(6-methoxy-1-methylbenzimidazol-2-ylmethoxy)benzyl]thiazolidine-2,4-dione, xiii) 5-[4-(5-hydroxy-1,4,6,7-tetramethylbenzimidazol-2-ylmethoxy)benzyl]thiazolidine-2,4-dione, xiv) 5-{4-[3-(5-methyl-2-phenyloxazol-4-yl)propionyl]benzyl}thiazolidine-2,4-dione, and xv) 5-[6-(2-fluorobenzyloxy)-2-naphthylmethyl]thiazolidine-2,4-dione;

and pharmaceutically acceptable salts thereof.

17. The method of claim 1, wherein said insulin sensitivity enhancer is selected from the group consisting of:

i) 5-[4-(6-hydroxy-2,5,7,8-tetramethylchroman-2-ylmethoxy)benzyl]thiazolidine-2,4-dione, ii) 5-{4-[2-(5-ethyl-2-pyridyl)ethoxy]benzyl}thiazolidine-2,4-dione, iii) 5-{4-[2-(N-methyl-N-pyrid-2-ylamino)ethoxy]benzyl}thiazolidine-2,4-dione, iv) 5-(4-{2-[1-(4-pyrid-2'-ylphenyl)ethylideneaminooxy]ethoxy}benzyl)thiazolidine-2,4-dione and v) 5-[4-(6-methoxy-1-methylbenzimidazol-2-ylmethoxy)benzyl]thiazolidine-2,4-dione;

and pharmaceutically acceptable salt thereof.

18. The method of claim 1, wherein said insulin sensitizer is 5-[4-(6-hydroxy-2,5,7,8-tetramethylchroman-2-ylmethoxy)benzyl]thiazolidine-2,4-dione or a pharmaceutically acceptable salt thereof.

19. The method of claim 1, wherein said insulin sensitizer is 5-{4-[2-(5-ethyl-2-pyridyl)ethoxy]benzyl}thiazolidine-2,4-dione or a pharmaceutically acceptable salt thereof.

20. The method of claim 1, wherein said insulin sensitizer is 5-{4-[2-(N-methyl-N-pyrid-2-ylamino)ethoxy]benzyl}thiazolidine-2,4-dione or a pharmaceutically acceptable salt thereof.

21. The method of claim 1, wherein said insulin sensitizer is 5-(4-{2-[1-(4-pyrid-2'-ylphenyl)ethylideneaminooxy]ethoxy}benzyl)thiazolidine-2,4-dione or a pharmaceutically acceptable salt thereof.

22. The method of claim 1, wherein said insulin sensitizer is 5-[4-(6-methoxy-1-methylbenzimidazol-2-ylmethoxy)benzyl]thiazolidine-2,4-dione or a pharmaceutically acceptable salt thereof.

23. A method for the treatment or prevention of hyperuricemia in a mammal in need thereof, which comprises administering to said mammal an amount of an insulin sensitivity enhancer effective to reduce or prevent hyperuricemia.

24. The method of claim 1, wherein the method is for the treatment of hyperuricemia in a human.

25. The method of claim 1, wherein the method is for the prevention of hyperuricemia in a human.

26. The method of claim 23, wherein the method is for the treatment of hyperuricemia in a mammal.

27. The method of claim 23, wherein the method is for the prevention of hyperuricemia in a mammal.

* * * * *